US010562883B2

(12) United States Patent
Hommes et al.

(10) Patent No.: US 10,562,883 B2
(45) Date of Patent: Feb. 18, 2020

(54) HETEROCYCLES CAPABLE OF MODULATING T-CELL RESPONSES, AND METHODS OF USING SAME

(71) Applicant: Nogra Pharma Limited, Dublin (IE)

(72) Inventors: Daan Hommes, Los Angeles, CA (US); Auke Verhaar, Gouda (NL); Gijs Van den Brink, Abcoude (NL); Francesca Viti, Salorino (CH)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 16/229,687

(22) Filed: Dec. 21, 2018

(65) Prior Publication Data

US 2019/0367480 A1    Dec. 5, 2019

Related U.S. Application Data

(63) Continuation of application No. 14/404,839, filed as application No. PCT/EP2013/061330 on May 31, 2013, now Pat. No. 10,208,017.

(60) Provisional application No. 61/654,385, filed on Jun. 1, 2012.

(51) Int. Cl.
| | | |
|---|---|---|
| C07D 239/26 | (2006.01) | |
| C07D 401/14 | (2006.01) | |
| H04L 12/26 | (2006.01) | |
| H04L 12/947 | (2013.01) | |
| C07D 213/36 | (2006.01) | |
| C07D 217/22 | (2006.01) | |
| C07D 239/38 | (2006.01) | |
| A61K 31/506 | (2006.01) | |

(52) U.S. Cl.
CPC .......... C07D 401/14 (2013.01); A61K 31/506 (2013.01); C07D 213/36 (2013.01); C07D 217/22 (2013.01); C07D 239/26 (2013.01); C07D 239/38 (2013.01); H04L 43/0894 (2013.01); H04L 49/251 (2013.01)

(58) Field of Classification Search
CPC .......................... C07D 239/26; A61K 31/4545
USPC .......................................... 544/242; 514/256
See application file for complete search history.

(56) References Cited

U.S. PATENT DOCUMENTS

| | | | |
|---|---|---|---|
| 5,332,745 | A | 7/1994 | Carter et al. |
| 6,753,327 | B1 | 6/2004 | Lubisch et al. |
| 8,093,246 | B2 | 1/2012 | Augeri et al. |
| 10,208,017 | B2 | 2/2019 | Hommes et al. |
| 2011/0077395 | A1 | 3/2011 | Li et al. |
| 2011/0294836 | A1 | 12/2011 | Song et al. |
| 2012/0184572 | A1 | 7/2012 | Song et al. |
| 2013/0158005 | A1 | 6/2013 | Heinrich et al. |
| 2015/0087673 | A1 | 3/2015 | Hitoshi et al. |
| 2015/0126553 | A1 | 5/2015 | Hommes et al. |
| 2016/0194303 | A1 | 7/2016 | Hommes et al. |
| 2016/0264548 | A1 | 9/2016 | Qiu et al. |
| 2017/0137430 | A1 | 5/2017 | Sandanayaka et al. |
| 2017/0183313 | A1 | 6/2017 | Hommes et al. |

FOREIGN PATENT DOCUMENTS

| | | |
|---|---|---|
| DE | 11 09 180 B | 6/1961 |
| EP | 2272828 A1 | 1/2011 |
| JP | 2008-013499 A | 1/2008 |
| SU | 1069385 A1 | 11/1990 |
| WO | WO-1998/045266 A1 | 10/1998 |
| WO | WO-00/073278 A2 | 12/2000 |
| WO | WO-2001/002409 A1 | 1/2001 |
| WO | WO-2003/035076 A1 | 5/2003 |
| WO | WO-2003/105779 A2 | 12/2003 |
| WO | WO-2004/084824 A2 | 10/2004 |
| WO | WO-2004/111014 A1 | 12/2004 |
| WO | WO-2005/118574 A1 | 12/2005 |
| WO | WO-2006/031806 A2 | 3/2006 |
| WO | WO-2006/097808 A1 | 9/2006 |
| WO | WO-2006/103399 A1 | 10/2006 |
| WO | WO-2006/113261 A2 | 10/2006 |
| WO | WO-2007/024680 A1 | 3/2007 |
| WO | WO-2007/084728 A2 | 7/2007 |
| WO | WO-2008/033834 A1 | 3/2008 |
| WO | WO-2008/036244 A1 | 3/2008 |
| WO | WO-2008/036882 A1 | 3/2008 |
| WO | WO-2008/082487 A2 | 7/2008 |
| WO | WO-2009/050248 A1 | 4/2009 |
| WO | WO-2009/109616 A2 | 9/2009 |
| WO | WO-2009/109654 A2 | 9/2009 |
| WO | WO-2010/007427 A1 | 1/2010 |
| WO | WO-2010/011756 A1 | 1/2010 |
| WO | WO-2010/017350 A1 | 2/2010 |
| WO | WO-2010/068806 A1 | 6/2010 |
| WO | WO-2010/118986 A1 | 10/2010 |
| WO | WO-2010/129802 A1 | 11/2010 |
| WO | WO-2010/146133 A1 | 12/2010 |
| WO | WO-2011/029807 A1 | 3/2011 |

(Continued)

OTHER PUBLICATIONS

Butini S et al., 2008, 'Exploiting Protein Fluctuations at the Active-site Gorge of Human Cholinesterases: Further Optimization of the Design Strategy to Develop Extremely Potent Inhibitors,' Med Chem, 51(11):3154-70.

CHEMCATS file; CAS Registry Number: 1060422-11-8; STN entry date: Oct. 13, 2008; chemical name: 4-[1-[(3,4-difluorophenyl)methyl]-3-piperidinyl]-2-[[2-(1-pyrrolidinyl)ethyl]thio]-pyrimidine.

CHEMCATS file; CAS Registry Number: 1061049-28-2; STN entry date: Oct. 14, 2008; chemical name: 4-[1-[(2,4-difluorophenyl)methyl]-3-piperidinyl]-2-[[2-(1-pyrrolidinyl)ethyl]thio]-pyrimidine.

(Continued)

Primary Examiner — Deepak R Rao
(74) Attorney, Agent, or Firm — Goodwin Procter LLP

(57) ABSTRACT

The present disclosure is directed in part to heterocycles, and their use in treating medical disorders, such as immune inflammatory disorders such as Crohn's disease, ulcerative colitis, rheumatic disorders, psoriasis, and allergies. The compounds are contemplated to modulate T-Cell responses.

14 Claims, 17 Drawing Sheets

(56) References Cited

FOREIGN PATENT DOCUMENTS

| WO | WO-2011/080568 A2 | 7/2011 |
|----|-------------------|--------|
| WO | WO-2011/101161 A1 | 8/2011 |
| WO | WO-2012/022408 A1 | 2/2012 |
| WO | WO-2013/131018 A1 | 9/2013 |
| WO | WO-2013/178815 A1 | 12/2013 |
| WO | WO-2013/178816 A1 | 12/2013 |

OTHER PUBLICATIONS

CHEMCATS file; CAS Registry Number: 1065547-98-9; STN entry date: Oct. 24, 2008; chemical name: 4-[1-[(3-fluorophenyl)methyl]-3-piperidinyl]-2-[[2-(1-pyrrolidinyl)ethyl]thio]-pyrimidine.

CHEMCATS file; CAS Registry Number: 1069500-17-9; STN entry date: Nov. 2, 2008; chemical name: 4-[1-[(2,6-difluorophenyl)methyl]-3-piperidinyl]-2-[[2-(1-pyrrolidinyl)ethyl]thio]-pyrimidine.

CHEMCATS file; CAS Registry Number: 1069509-60-9; STN entry date: Nov. 2, 2008; chemical name: 2-[[2-(1-pyrrolidinyl)ethyl]thio]-4-[1-[[3-(trifluoromethyl)phenyl]methyl]-3-piperidinyl]-pyrimidine.

CHEMCATS file; CAS Registry Number: 1208856-17-0; STN entry date: Mar. 11, 2010; chemical name: 4-[1-[(2-fluorophenyl)methyl]-3-piperidinyl]-2-[[2-(1-pyrrolidinyl)ethyl]thio]-pyrimidine.

Danagulyan GG et al., 1990, 'Formation of Condensation Side Product in the Synthesis of 2-Benzyl-4-Methyl-6-Chloropyrimidine,' Chem Heterocycl Comp, 26(6):711-2.

De la Hoz A et al., 2002, 'Solvent-Free Synthesis and Structural Characterization of Azolyl-Substituted Pyrimidines,' New J Chem, 26(7):926-32.

Eun-Kyung S et al., 2006, 'Porphyrins Bearing Stable meso-Alkylidenyl Double Bonds. A New Family of Nonplanar Porphyrinoids,' Org Lett, 8,(15):3355-8.

European Patent Office Communication Pursuant to Article 94(3) EPC, Application No. 13 726 006 dated Jan. 4, 2017 (9 pages).

Guajardo RJ et al., 1995, 'Structural Features that Control Oxygen Activation at the Non-Heme iron Site in Fe(II)-Bleomysin: An Analogue Study,' J Am Chem Soc, 117(13):3883-4.

Hayes ME et al., 2008, Lead Identification of 2-Iminobenzimidazole Antagonists of the Chemokine Receptor CXCR3, Bioorg Med Chemi Lett, 18(7):2414-9.

Herfeldt VG, 1986, 'Zur Kenntniss der Kyanalkine Insbesondere des Kyanbezylins,' J Für Praktische Chemie, 53(1):246-50 (Compounds on pp. 246 and 250 only).

Herrera A et al., 2002, 'On the Mechanism of Reaction Between Ketones and Nitriles. Unexpected Results from Benzyl Nitriles,' Tetrahedron, 58(19):3755-64.

Herrera A et al., 2003, 'One-Pot Synthesis of New Heterocycles: 2,4-Disubstituted 6,7-Dihydro-5H-benzo[6,7]Cyclohepta[1,2-d]Pyrimidines,' Tetrahedron Lett, 44(10):2149-51.

Herrera A et al., 2006, 'The Reaction of Tetralones with Nitriles: A Simple Approach to the Synthesis of New Substituted Benzo[h]quinazolines, Benzo[f]quinazolines and Dibenzo[a,i]phenanthridines,' Tetrahedron, 62(12):2799-811.

Hocek M et al., 2003, 'Synthesis of Carba-Analogues of Myoseverin by Regioselective Cross-Coupling Reactions of 2,6-dichloro-9-isopropylpurine,' Tetrahedron, 59(5):607-11.

Holloway GA et al., 2007, 'Discovery of 2-Iminobenzimadazoles as a New Class of Trypanothione Reductase Inhibitor by High-Throughput Screening,' Bioorg Med Chem Lett, 17(5):1422-7.

International Preliminary Report on Patentability and Written Opinion of the International Searching Authority for PCT/EP2013/061328 dated Dec. 2, 2014 (8 pages).

International Preliminary Report on Patentability and Written Opinion of the International Searching Authority for PCT/EP2013/061330 dated Dec. 2, 2014 (14 pages).

International Search Report of the International Searching Authority for PCT/EP2013/061328 dated Jul. 9, 2013 (5 pages).

International Search Report of the International Searching Authority for PCT/EP2013/061330 dated Sep. 2, 2013 (15 pages).

Kato T and Yamamoto Y, 1967, 'Studies on Ketene and Its Derivatives. XVII. Reaction of Diketene with Imidates,' Chem Pharm Bull (Tokyo), 15(9):1334-8.

Krupková S et al., 2010, 'Synthesis of Quinazolines from N-(2-Nitrophenylsulfonyl)iminodiacetate and α-(2-Nitrophenylsulfonyl)amino Ketones via 2H-Indazole 1-Oxides,' J Org Chem, 75(13):4562-6.

Miyagawa N et al., 2010, 'Successive Catalytic Reactions Specific to Pd-Based Rotaxane Complexes as a Result of Wheel Translation Along the Axle,' Chem Comm, 46(11):1920.

Murray TP et al., 1974, 'Dimetalated Heterocycles as Synthetic Intermediates. V. Dianions Derived from Certain 2-Hydroxy-4-Methylpyrimidines, 2-Amino-4-Methylpyrimidines, and Related Compounds,' J Org Chem, 39(5):595-600.

Mysliborski R et al., 2006, 'Pyriporphyrin-A Porphyrin Homologue Containing a Built-in Pyridine Moiety,' Eur J Org Chem, 2006(14):3064-8.

Mysliborski R et al., 2006, Subpyriporphyrin-A [14]Triphyrin (1.1.1) Homologue with an Embedded Pyridine Moiety, Angew Chem Int Edit, 45(22):3670-4.

Olea-Azar C et al., 2008, 'ESR, Electrochemical and Cyclodextrin-inclusion Studies of Triazolopyridyl Pyridyl Ketones and Dipyridyl Ketones Derivatives,' Spectrochim Acta Mol Biomol Spectrosc, 71(2):703-9.

Pace P et al., 2007, 'Dihydroxypyrimidine-4-Carboxamides as Novel Potent and Selective HIV Integrade Inhibitors,' Med Chem, 50(9):2226-9.

Purandare AV et al,, 2005, Identification of Chemokine Receptor CCR4 Antagonist, Bioorg Med Chem Lett, 15(10):2669-72.

Rautio J et al., 2008, 'Prodrugs: Design and Clinical Applications,' Nat Rev Drug Disc, 7(3):255-70.

Richardson T et al., 1937, 'Synthetical Experiments in the Chelidonine-Sanguinarine Group of the Alkaloids. Part I,' J Chem Soc (Resumed), 1(1):835-41.

Simplício AL et al.,2008, 'Prodrugs for Amines,' Molecules, 13(3):519-47.

Smirnov LD et al., 2005, 'Synthesis of 3-Hydroxy-6-Methyl- and 3-Hydroxy-2-(2-Phenylethyl)Pyridines and Their Sulfur-Containing Amino and Hydroxymethyl Derivatives,' Chem Heterocycl Comp, 41(8):1013-8.

STN Registry, 2008, 'Pyrimidine, 4-[1-[(3,5-difluorophenyl)methyl]-3-piperidinyl]-2-[[2-(1-pyrrolidinyl)ethyl]thio],' RN# 1069767-68-5, Chemical Library, ChemBridge Corporation, San Diego, CA (Supplier).

Summa V et al., 2006, '4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species,' Med Chem, 49(23):6646-9.

Suzuki Y et al., 1998, 'Carbon-Carbon Bond Cleavage of α-Hydroxybenzylheteroarenes Catalyzed by Cyanide Ion : Retro-Benzoin Condensation Affords Ketones and Heteroarenes and Benzyl Migration Affords Benzylheteroarenes and Arenecarbaldehydes,' Chem Pharm Bull (Tokyo), 46(2):199-206.

Varma RS et al., 1985, 'Synthesis of 5-methoxy-1,3-disubstituted-benzimidazolin-2-thiones as Potential Biologically Active Agents,' J Indian Chem Soc, 62:73-5.

Wang H, et al., 2008, 'Pyridine amides as Potent and selective Inhibitors of 11β-hydroxysteroid Dehydrogenase Type 1,' Bioorg Med Chem Lett, 18(11):3170-1.

Yamamoto Y et al., 1995, 'Direct Introduction of Acyl and Ethoxycarbonyl Groups into Pyrimidine Ring through the Trimethylstannyl Derivatives,' Heterocycles, 41(6):1275-90.

Zhang H-C et al., 2001, 'Discovery and Optimization of a Novel Series of Thrombin Receptor (PAR-1) Antagonists: Potent, Selective Peptide Mimetics Based on Indole and Indazole Templates,' J Med Chem, 44(7):1021-4.

Zhang Y-X et al., 2004, 'Enantiospecific Synthesis of Pyridinylmethyl Pyrrolidinemethanols and Catalytic Asymmetric Borane Reduction of Prochiral Ketones,' Tetrahedron-Asymmetr, 15(1):177-82.

(56) References Cited

OTHER PUBLICATIONS

Zielinski W, 1985, 'Preparation of Pyrimidines and Pyridines from Alkyl Ketones and Nitriles in Presence of Phosphoryl Chloride,' Heterocycles, 23(7):1639-44.
U.S. Appl. No. 14/404,839, Heterocycles Capable of Modulating T-Cell Responses, and Methods of Using Same, filed Dec. 1, 2014, Patented, U.S. Pat. No. 10,208,017.

HETEROCYCLES CAPABLE OF MODULATING T-CELL RESPONSES, AND METHODS OF USING SAME

RELATED APPLICATIONS

This application is a continuation patent application of U.S. patent application Ser. No. 14/404,839, filed on Dec. 1, 2014, which application is a U.S. national stage application of International Application No. PCT/EP2013/061330, filed on May 31, 2013, which application claims priority to and the benefit of U.S. Provisional Patent Application No. 61/654,385, filed on Jun. 1, 2012; the contents of each of which are incorporated by reference herein in their entirety.

BACKGROUND

T lymphocytes (i.e., T cells) are a group of white blood cells that play a major role in cell-mediated immunity. T lymphocytes are activated through the T-Cell Receptor (TCR), a cell type specific receptor. When the TCR is stimulated, another T cell specific protein called lymphocyte-specific protein tyrosine kinase (LCK) is recruited. After recruitment of LCK, a specific signaling cascade is activated, ultimately resulting in the proliferation and production of cytokines (e.g., immunomodulating agents, such as interleukins and interferons).

There are two main subsets of T lymphocytes that are distinguished by the presence of cell surface molecules CD4 and CD8. The T lymphocytes expressing CD4 are regarded as being major cytokine producers. The CD4 subset can be further divided into Th1 and Th2, and the cytokines they produce are known as Th1-type cytokines and Th2-type cytokines.

Chronic immune inflammatory diseases such as rheumatoid arthritis and Crohn's disease are disorders associated with a Th1 response. Th1 cytokines such as interferon gamma tend to produce the pro-inflammatory responses responsible for killing intracellular parasites and for perpetuating autoimmune responses. The response involves recruitment of activated T lymphocytes which infiltrate local tissue causing damage to it. Excessive pro-inflammatory responses can lead to uncontrolled tissue damage, so there needs to be a counteracting mechanism.

The glucocorticoids (GCs) are steroid hormones that act as powerful immunosuppressive drugs, suppressing inflammation on many levels. GCs can passively cross the cellular membrane and bind their cognate receptor, which then moves into the nucleus where it binds DNA and regulates specific genes. Although this is considered to be the main mechanism of action, GC treatment also causes rapid effects on signaling molecules and pathways, for example, by the inhibition of TCR-related signaling. GC treatment causes disruption of a complex of proteins, including the TCR, LCK and the glucocorticoid receptor (GR), and as a consequence downstream signaling is inhibited and proliferation stops. The treatment often results in severe side effects. However, alternative ways of T cell stimulation, which cause activation of alternative signaling pathways, may also lead to proliferation that can not be inhibited by GCs.

There is an unmet need for new therapies to treat immune inflammatory disorders.

SUMMARY

Provided herein are compounds contemplated to be T-Cell receptor modulators, and their use as, for example, medicinal agents. Accordingly, one aspect of the disclosure provides a compound of Formula I:

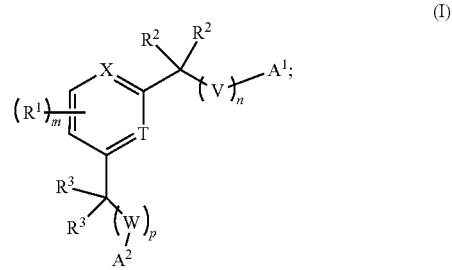

Formula IA, IB, IC, or ID:

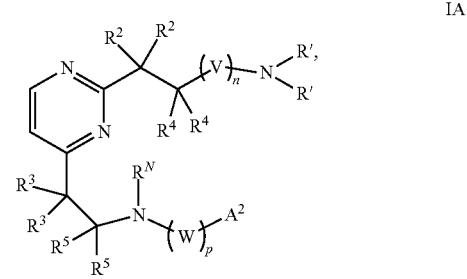

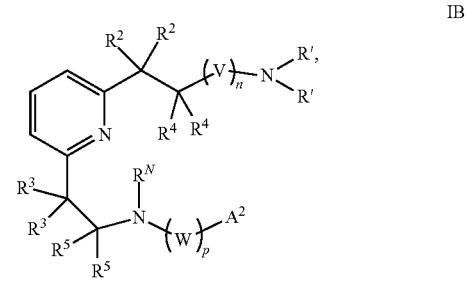

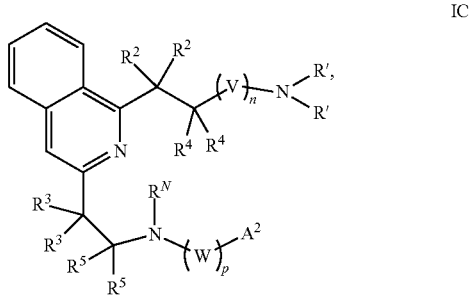

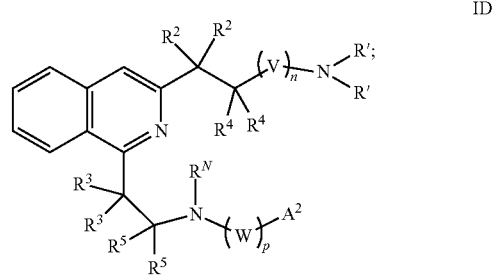

Formula IE, IF, IG, or IH:

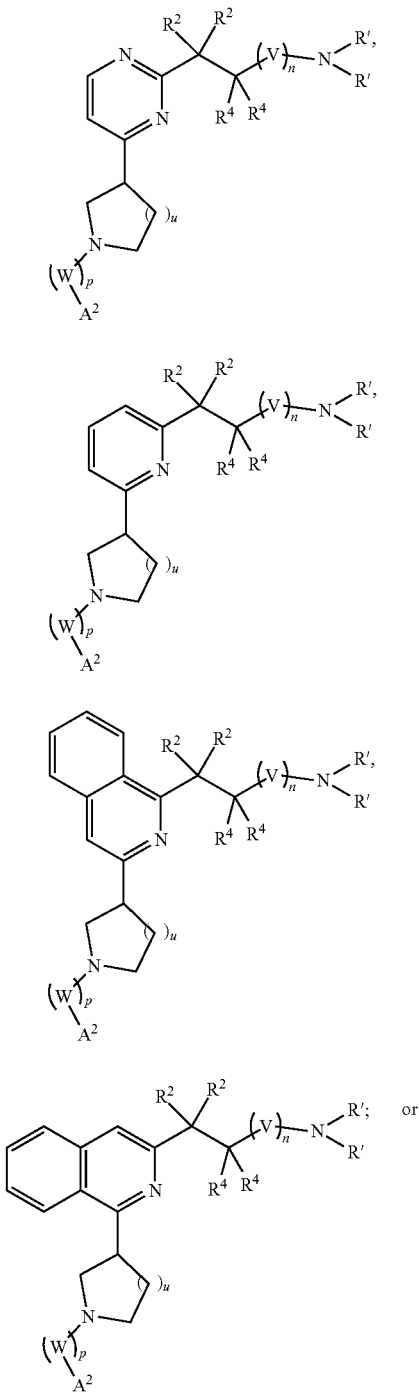

a pharmaceutically acceptable salt thereof, wherein the variables are as defined in the detailed description.

Also provided herein are methods of treating a disease or disorder selected from the group consisting of colitis, Crohn's disease, and cancer, comprising administering a pharmaceutically effective amount of a heterocyclic compound described herein, e.g., a compound of Formula I, IA, IB, IC, ID, IE, IF, IG, IH, or II.

DETAILED DESCRIPTION

Figure 1A:
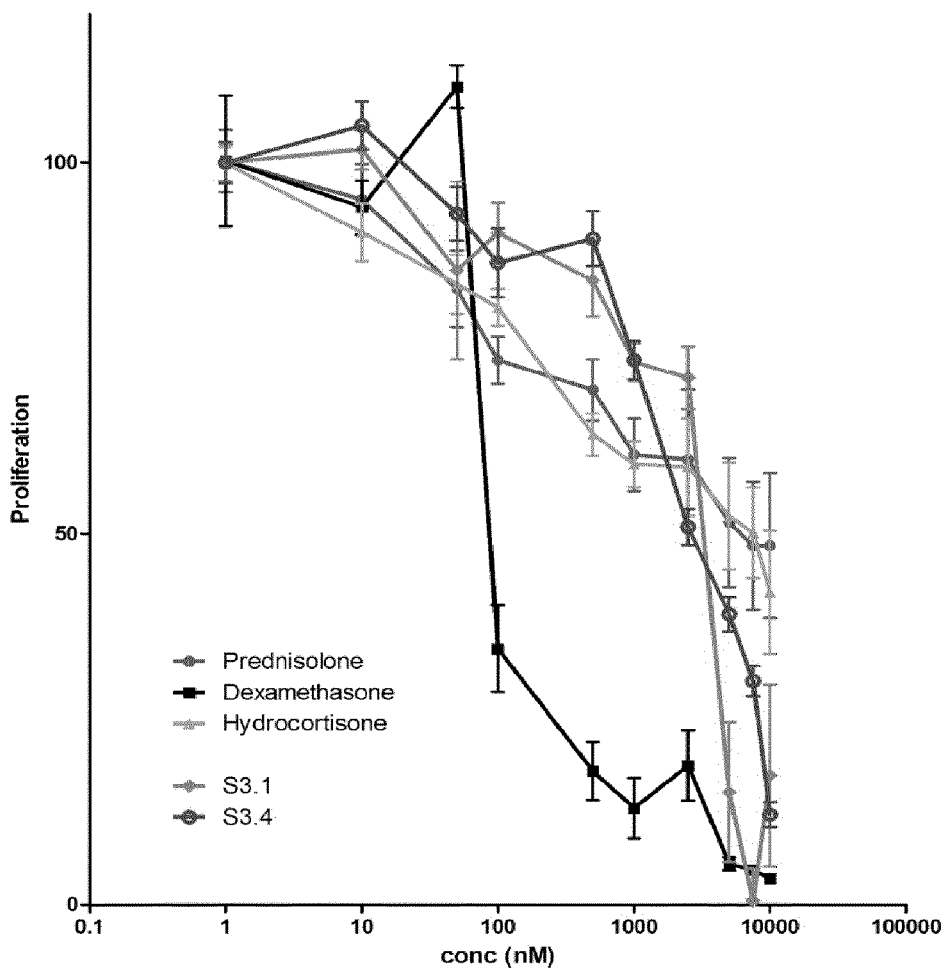
FIGS. 1A, 1B and 1C depict the effect of disclosed compounds on T lymphocyte proliferation.

The disclosure is based, in part, upon the discovery that certain compounds disclosed herein have the ability to modulate the activity of T-cell receptors.

Before further description, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the group —C(O)—.

The term "cyano" as used herein refers to the group —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the group —OH.

The term "oxo" as used herein refers to the group =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, e.g., mice, rats, other rodents, rabbits, dogs, cats, swine, cattle, sheep, horses, or primates, and humans. In an embodiment, the patient is a human. The compounds contemplated herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods contemplated herein is desirably a mammal in which treatment of obesity or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal (e.g., mammal or human) that is being sought by the researcher, veterinarian, medical doctor or other clinician. The compounds contemplated herein are administered in therapeutically effective amounts to treat a disease or disorder. Alternatively, a therapeutically effective amount of a compound is the quantity required to achieve a desired therapeutic and/or prophylactic effect, such as an amount, which results in weight loss.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present disclosure encompasses various stereoisomers of these compounds and mixtures thereof. Mixtures of enantiomers or diastereomers may be designated "(±)" in nomenclature, but the skilled artisan will recognize that a structure may denote a chiral center implicitly.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, Classics in Stereoselective Synthesis, Wiley-VCH: Weinheim, 2009.

The compounds disclosed herein can exist in solvated as well as unsolvated forms with pharmaceutically acceptable solvents such as water, ethanol, and the like, and it is intended that the disclosure embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The disclosure also embraces isotopically labeled compounds of the disclosure which are identical to those recited herein, except that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes may be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds contemplated herein can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). In one embodiment, the transformation may be by, for example, chemical hydrolysis or enzymatic attack. Prodrugs are well known in the art (for example, see Rautio, Kumpulainen, et al., Nature Reviews Drug Discovery 2008, 7, 255). For example, if a compound contemplated herein or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound contemplated herein contains an alcohol functional group, a prodrug can be formed by the replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl ($C_{1-6}$) alkoxycarbonyloxymethyl, N—($C_{1-6}$)alkoxycarbonylaminomethyl, succinoyl, ($C_{1-6}$)alkanoyl, α-amino($C_{1-4}$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_{1-6}$)alkyl)$_2$ or glycosyl (the radical resulting from the removal of a hydroxyl group of the hemiacetal form of a carbohydrate).

If a compound contemplated herein incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein.

A derivative or pro-drug can have enhanced permeability for a target organ. The prodrug has an enhanced permeability according to the present disclosure if, after administration of the pro-drug or derivative thereof to a living organism, a higher amount of the compound reaches the target organ, resulting in a higher level of effective agent, as compared to administration of the base compound without derivatization.

Further, if a variable is not accompanied by a definition, then the previous definition of the variable controls.

T Cell Receptor Ligands

In another aspect, a heterocyclic compound of Formula I is provided:

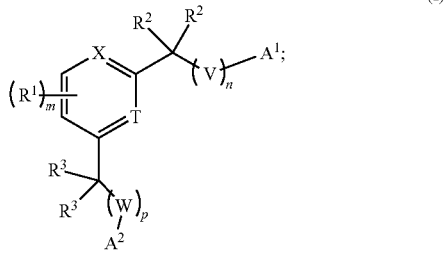

(I)

wherein $A^1$ is selected from the group consisting of $C_{3-6}$cycloalkyl, heterocyclyl, phenyl, naphthyl, heteroaryl, —NR' R', —U—$C_{3-6}$cycloalkyl, —U-heterocyclyl, —U-phenyl, —U-naphthyl, —U-heteroaryl, phenylalkyl, naphthylalkyl, heterocycloalkyl, and heteroarylalkyl; wherein $C_{3-6}$cycloalkyl, heterocyclyl, phenyl, naphthyl, and heteroaryl are optionally substituted with one, two, three or more substituents each selected from $R^{A1}$;

$A^2$ is selected from the group consisting of $C_{3-6}$cycloalkyl, heterocyclyl, phenyl, naphthyl, heteroaryl, $C_{1-6}$alkyl, hydroxy, —NR'R', —O—$C_{1-6}$alkyl, —S—$C_{1-6}$alkyl, —U—$C_{3-6}$cycloalkyl, —U-heterocyclyl, —U-phenyl, —U-naphthyl, —U-heteroaryl, phenylalkyl, naphthylalkyl, heterocycloalkyl, and heteroarylalkyl; wherein $C_{3-6}$cycloalkyl, heterocyclyl, phenyl, naphthyl, heteroaryl, and $C_{1-6}$alkyl are optionally substituted with one, two, three or more substituents each selected from $R^{A2}$;

U is selected from the group consisting of —S—, —NR'—, —O—, or $C_{1-6}$alkyl;

T is selected from the group consisting of CH, CR$^1$ or N;

X is selected from the group consisting of CH, CR$^1$ or N;

V is independently selected, for each occurrence, from the group consisting of O, S, NR', and CR$^4$R$^4$;

W is independently selected, for each occurrence, from the group consisting of O, S, NR', and CR$^5$R$^5$;

$R^1$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, cyano, nitro, alkoxy, $C_{3-6}$cycloalkyl, heterocyclyl, heteroaryl and phenyl;

or two $R^1$ substituents may be taken together with the atoms to which they are attached to form a saturated, partially saturated or unsaturated, 4-6 membered aliphatic or heterocyclic ring;

$R^2$, $R^3$, $R^4$ and $R^5$ are independently selected, for each occurrence, from the group consisting of hydrogen, halogen, hydroxyl, amino, amido, sulfonyl, sulfonamide, thiol, $C_{1-6}$alkyl, halo$C_{1-6}$alkyl, carboxyl, cyano, nitro, alkoxy, $C_{3-6}$cycloalkyl, heterocyclyl, phenyl, naphthyl, and heteroaryl;

or two $R^2$ substituents, two $R^3$ substituents, two $R^4$ substituents or two $R^5$ substituents may be taken together to form an oxo, imino or sulfanylidene;

or two $R^2$ substituents, two $R^3$ substituents, two $R^4$ substituents, or two $R^5$ substituents may be taken together with the atom or atoms to which they are attached to form a $C_{3-6}$cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

or one $R^2$ substituent and one $R^4$ substituent or one $R^3$ substituent and one $R^5$ substituent may be taken together with the atoms to which they are attached to form a $C_{3-6}$cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

$R^{A1}$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, cyano, nitro, alkoxy, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, oxo, $C_{3-6}$cycloalkyl, heterocyclyl, heteroaryl and phenyl;

$R^{A2}$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, cyano, nitro, alkoxy, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, oxo, $C_{3-6}$cycloalkyl, heterocyclyl, heteroaryl and phenyl;

R' is independently selected, for each occurrence, from the group consisting of hydrogen or $C_{1-6}$alkyl; wherein $C_{1-6}$alkyl is optionally substituted with one, two, three or more substituents each selected from $R^{A2}$;

or two R' may be taken together with the nitrogen to which they are attached to form a saturated, partially saturated or unsaturated, 4-7 membered monocyclic or 10-15 membered bicyclic heterocycle having one, two or three heteroatoms independently selected from the group consisting of N, O, and S;

or a R' substituent and a $R^2$, $R^3$, $R^4$ or $R^5$ substituent may be taken together with the atoms to which they are attached to form a saturated, partially saturated or unsaturated, 4-6 membered monocyclic or 10-12 membered bicyclic heterocycle having one, two or three heteroatoms independently selected from the group consisting of N, O, and S;

n is selected from the group consisting of 0, 1, 2, 3 and 4;

p is selected from the group consisting of 0, 1, 2, 3 and 4;

m is selected from the group consisting of 0, 1, or 2; or pharmaceutically acceptable salts or stereoisomers thereof.

In some embodiments, X and T may be N. In another embodiment, X may be CR' and T may be N.

In one embodiment, $A^1$ may be selected from the group consisting of $C_{3-6}$cycloalkyl, heterocyclyl, phenyl, naphthyl, heteroaryl, and —NR'R'.

In another embodiment, $A^2$ may be selected from the group consisting of $C_{3-6}$cycloalkyl, phenyl, and naphthyl.

In certain embodiments, V may be $CH_2$.

In an embodiment, W may be independently selected, for each occurrence, from the group consisting of O, S, NR', $CH_2$ and C(O).

In other embodiments, p may be selected from the group consisting of 1 and 2; and wherein at least one W is NR'.

In some embodiments, one $R^3$ substituent and the R' substituent of W may be taken together with the atoms to which they are attached to form a saturated, partially saturated or unsaturated, 4-6 membered monocyclic or 10-12 membered bicyclic heterocycle having one, two or three heteroatoms independently selected from the group consisting of N, O, and S.

In one embodiment, $R^2$ and $R^3$ may be hydrogen.

In another embodiment, n may be selected from the group consisting of 1 and 2.

In another aspect, a heterocyclic compound of Formula IA, IB, IC or ID is provided:

IA
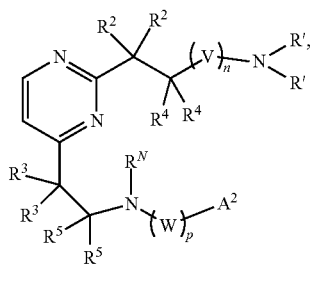

IB
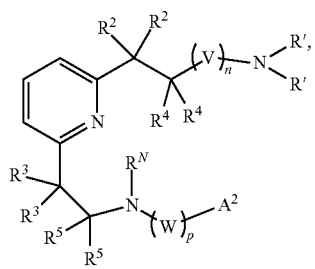

IC
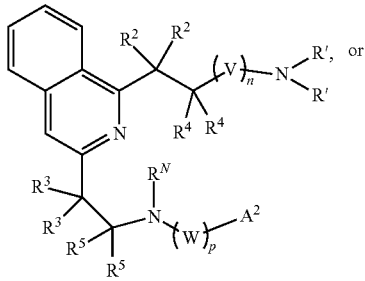

ID
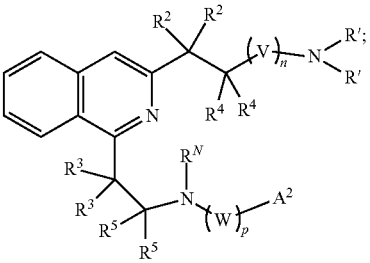

wherein $A^2$ is selected from the group consisting of $C_{3-6}$cycloalkyl, heterocyclyl, phenyl, naphthyl, heteroaryl, $C_{1-6}$alkyl, hydroxy, —NR'R', —O—$C_{1-6}$alkyl, —S—$C_{1-6}$alkyl, —U—$C_{3-6}$cycloalkyl, —U-heterocyclyl, —U-phenyl, —U-naphthyl, —U-heteroaryl, phenylalkyl, naphthylalkyl, heterocycloalkyl, and heteroarylalkyl; wherein $C_{3-6}$cycloalkyl, heterocyclyl, phenyl, naphthyl, heteroaryl, and $C_{1-6}$alkyl are optionally substituted with one, two, three or more substituents each selected from $R^{A2}$;

U is selected from the group consisting of —S—, —NR'—, —O—, or $C_{1-6}$alkyl;

V is $CR^4R^4$;

W is $CR^5R^5$;

$R^2$, $R^3$, $R^4$ and $R^5$ are independently selected, for each occurrence, from the group consisting of hydrogen, halogen, hydroxyl, amino, amido, sulfonyl, sulfonamide, thiol, $C_{1-6}$alkyl, halo$C_{1-6}$alkyl, carboxyl, cyano, nitro, alkoxy, $C_{3-6}$cycloalkyl, heterocyclyl, phenyl, naphthyl, and heteroaryl;

or two $R^2$ substituents, two $R^3$ substituents, two $R^4$ substituents or two $R^5$ substituents may be taken together to form an oxo, imino or sulfanylidene;

or two $R^2$ substituents, two $R^3$ substituents, two $R^4$ substituents, or two $R^5$ substituents may be taken together with the atom or atoms to which they are attached to form a cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

or one $R^2$ substituent and one $R^4$ substituent or one $R^3$ substituent and one $R^5$ substituent may be taken together with the atoms to which they are attached to form a cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

$R^{A2}$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, cyano, nitro, alkoxy, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, oxo, $C_{3-6}$cycloalkyl, heterocyclyl, heteroaryl and phenyl;

$R^N$ is selected from the group consisting of hydrogen or $C_{1-6}$alkyl; wherein $C_{1-6}$alkyl is optionally substituted with one, two, three or more substituents each selected from $R^{A2}$;

or $R^N$ may be taken together with a $R^3$ or $R^5$ substituent and the atoms to which they are attached to form a saturated, partially saturated or unsaturated, 4-6 membered monocyclic or 10-12 membered bicyclic heterocycle having one, two or three heteroatoms independently selected from the group consisting of N, O, and S;

R' is independently selected, for each occurrence, from the group consisting of hydrogen or $C_{1-6}$alkyl; wherein $C_{1-6}$alkyl is optionally substituted with one, two, three or more substituents each selected from $R^{A2}$;

or two R' substituents may be taken together with the nitrogen to which they are attached to form a saturated, partially saturated or unsaturated, 4-7 membered monocyclic or 10-15 membered bicyclic heterocycle having one, two or three heteroatoms independently selected from the group consisting of N, O, and S;

or a R' substituent and a $R^4$ substituent may be taken together with the nitrogen to which they are attached to form a saturated, partially saturated or unsaturated, 4-7 membered monocyclic or 10-15 membered bicyclic heterocycle having one, two or three heteroatoms independently selected from the group consisting of N, O, and S;

n is selected from the group consisting of 0, 1, 2, 3 and 4;

p is selected from the group consisting of 0, 1, 2, 3 and 4;

or pharmaceutically acceptable salts or stereoisomers thereof.

In one embodiment, V may be $CH_2$.

In some embodiments, n may be selected from the group consisting of 0 and 1.

In other embodiments,

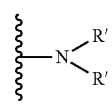

may be selected from the group consisting of:

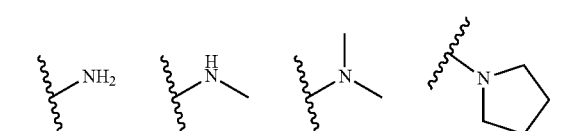

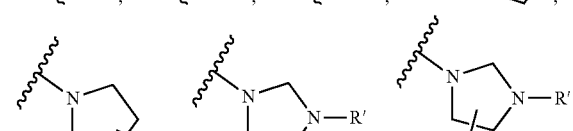

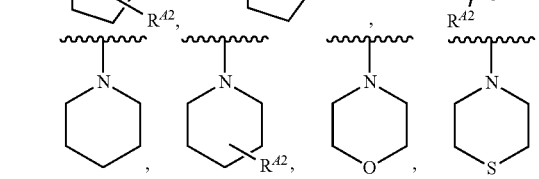

or any pharmaceutically acceptable salts thereof.

In certain embodiments, $A^2$ may be selected from the group consisting of $C_{3-6}$cycloalkyl, phenyl, and naphthyl.

In one embodiment, W may be $CH_2$.

In another embodiment, p may be selected from the group consisting of 0 and 1.

In some embodiments, one $R^3$ substituent and the $R^N$ substituent are taken together with the atoms to which they are attached to form a saturated, partially saturated or unsaturated, 4-6 membered monocyclic or 10-12 membered bicyclic heterocycle having one, two or three heteroatoms independently selected from the group consisting of N, O, and S.

In another aspect, a heterocyclic compound of Formula IE, IF, IG or IH is provided:

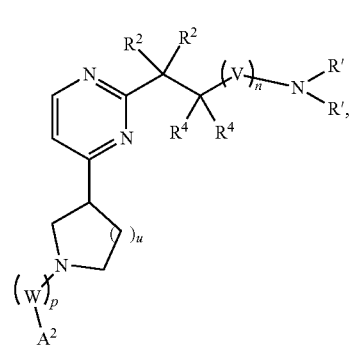

IE

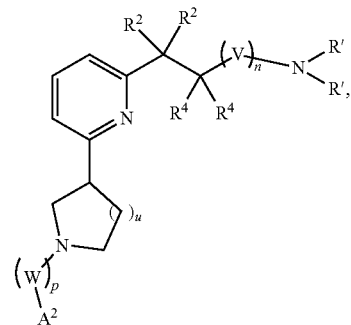

IF

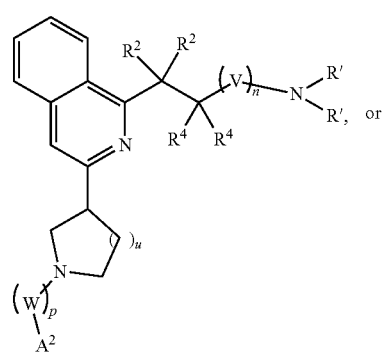

IG

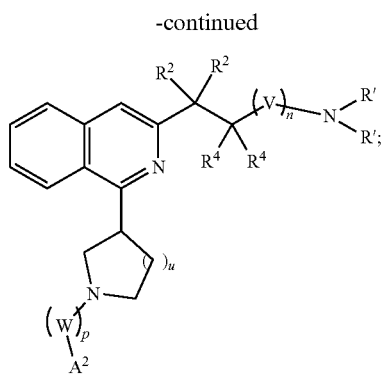

wherein
$A^2$ is selected from the group consisting of $C_{3-6}$cycloalkyl, heterocyclyl, phenyl, naphthyl, heteroaryl, $C_{1-6}$alkyl, hydroxy, —NR'R', —O—$C_{1-6}$alkyl, —S—$C_{1-6}$alkyl, —U—$C_{3-6}$cycloalkyl, —U-heterocyclyl, —U-phenyl, —U-naphthyl, —U-heteroaryl, phenylalkyl, naphthylalkyl, heterocycloalkyl, and heteroarylalkyl; wherein cycloalkyl, heterocyclyl, phenyl, naphthyl, heteroaryl, and $C_{1-6}$alkyl are optionally substituted with one, two, three or more substituents each selected from $R^{A2}$;

U is selected from the group consisting of —S—, —NR'—, —O—, or $C_{1-6}$alkyl;

V is $CR^4R^4$;

W is $CR^5R^5$;

$R^2$, $R^4$ and $R^5$ are independently selected, for each occurrence, from the group consisting of hydrogen, halogen, hydroxyl, amino, amido, sulfonyl, sulfonamide, thiol, $C_{1-6}$alkyl, halo$C_{1-6}$alkyl, carboxyl, cyano, nitro, alkoxy, $C_{3-6}$cycloalkyl, heterocyclyl, phenyl, naphthyl, and heteroaryl;

or two $R^2$ substituents, two $R^4$ substituents or two $R^5$ substituents may be taken together to form an oxo, imino or sulfanylidene;

or two $R^2$ substituents, two $R^4$ substituents, or two $R^5$ substituents may be taken together with the atom or atoms to which they are attached to form a cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

or one $R^2$ substituent and one $R^4$ substituent may be taken together with the atoms to which they are attached to form a cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

$R^{A2}$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, cyano, nitro, alkoxy, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, oxo, $C_{3-6}$cycloalkyl, heterocyclyl, heteroaryl and phenyl;

R' is independently selected, for each occurrence, from the group consisting of hydrogen or $C_{1-6}$alkyl; wherein $C_{1-6}$alkyl is optionally substituted with one, two, three or more substituents each selected from $R^{A2}$;

or two R' substituents may be taken together with the nitrogen to which they are attached to form a saturated, partially saturated or unsaturated, 4-7 membered monocyclic or 10-15 membered bicyclic heterocycle having one, two or three heteroatoms independently selected from the group consisting of N, O, and S;

or a R' substituent and a $R^4$ substituent may be taken together with the nitrogen to which they are attached to form a saturated, partially saturated or unsaturated, 4-7 membered monocyclic or 10-15 membered bicyclic heterocycle having one, two or three heteroatoms independently selected from the group consisting of N, O, and S;

n is selected from the group consisting of 0, 1, 2, 3 and 4;
p is selected from the group consisting of 0, 1, 2, 3 and 4;
u is selected from the group consisting of 0, 1, 2 or 3; or pharmaceutically acceptable salts or stereoisomers thereof.

In one embodiment, V may be $CH_2$.

In another embodiment, n may be selected from the group consisting of 0 and 1.

In certain embodiments,

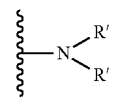

may be selected from the group consisting of:

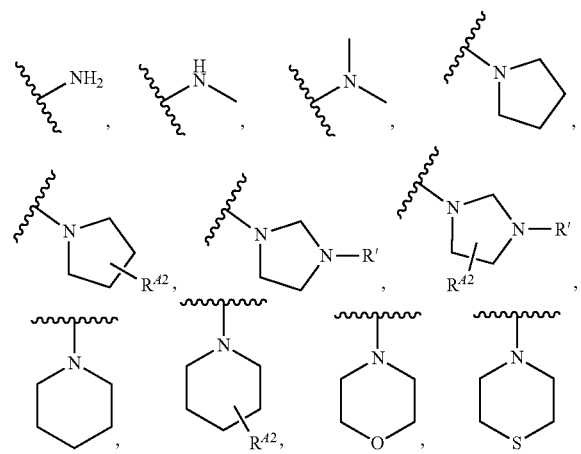

or any pharmaceutically acceptable salts thereof.

In other embodiments, $A^2$ may be selected from the group consisting of $C_{3-6}$cycloalkyl, phenyl, and naphthyl.

In some embodiments, W may be $CH_2$.

In another embodiment, p may be selected from the group consisting of 0 and 1.

In one aspect, a heterocyclic compound of Formula II is provided:

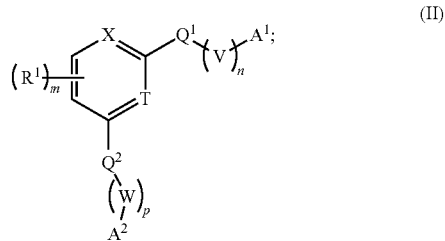

wherein

A¹ is selected from the group consisting of $C_{3-6}$cycloalkyl, heterocyclyl, phenyl, naphthyl, heteroaryl, —NR'R', —U—$C_{3-6}$cycloalkyl, —U-heterocyclyl, —U-phenyl, —U-naphthyl, —U-heteroaryl, phenylalkyl, naphthylalkyl, heterocycloalkyl, and heteroarylalkyl; wherein $C_{3-6}$cycloalkyl, heterocyclyl, phenyl, naphthyl, and heteroaryl are optionally substituted with one, two, three or more substituents each selected from $R^{41}$;

A² is selected from the group consisting of $C_{3-6}$cycloalkyl, heterocyclyl, phenyl, naphthyl, heteroaryl, $C_{1-6}$alkyl, hydroxy, —NR'R', —O—$C_{1-6}$alkyl, —S—$C_{1-6}$alkyl, —U—$C_{3-6}$cycloalkyl, —U-heterocyclyl, —U-phenyl, —U-naphthyl, —U-heteroaryl, phenylalkyl, naphthylalkyl, heterocycloalkyl, and heteroarylalkyl; wherein $C_{3-6}$cycloalkyl, heterocyclyl, phenyl, naphthyl, heteroaryl, and $C_{1-6}$alkyl are optionally substituted with one, two, three or more substituents each selected from $R^{42}$;

U is selected from the group consisting of —S—, —NR'—, —O—, or $C_{1-6}$alkyl;

T is selected from the group consisting of CH, $CR^1$ or N;

X is selected from the group consisting of CH, $CR^1$ or N;

$Q^1$ is independently selected, for each occurrence, from the group consisting of O, S, NR', and $CR^2R^2$;

$Q^2$ is independently selected, for each occurrence, from the group consisting of O, S, NR', and $CR^3R^3$;

V is independently selected, for each occurrence, from the group consisting of O, S, NR', and $CR^4R^4$;

W is independently selected, for each occurrence, from the group consisting of O, S, NR', and $CR^5R^5$;

$R^1$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, cyano, nitro, alkoxy, $C_{3-6}$cycloalkyl, heterocyclyl, heteroaryl and phenyl;

or two $R^1$ substituents may be taken together with the atoms to which they are attached to form a saturated, partially saturated or unsaturated, 4-6 membered aliphatic or heterocyclic ring;

$R^2$, $R^3$, $R^4$ and $R^5$ are independently selected, for each occurrence, from the group consisting of hydrogen, halogen, hydroxyl, amino, amido, sulfonyl, sulfonamide, thiol, $C_{1-6}$alkyl, halo$C_{1-6}$alkyl, carboxyl, cyano, nitro, alkoxy, $C_{3-6}$cycloalkyl, heterocyclyl, phenyl, naphthyl, and heteroaryl;

or two $R^2$ substituents, two $R^3$ substituents, two $R^4$ substituents or two $R^5$ substituents may be taken together to form an oxo, imino or sulfanylidene;

or two $R^2$ substituents, two $R^3$ substituents, two $R^4$ substituents, or two $R^5$ substituents may be taken together with the atom or atoms to which they are attached to form a $C_{3-6}$cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

or one $R^2$ substituent and one $R^4$ substituent or one $R^3$ substituent and one $R^5$ substituent may be taken together with the atoms to which they are attached to form a $C_{3-6}$cycloalkyl, phenyl, naphthyl, or a saturated, partially saturated or unsaturated, 4-6 membered monocyclic or 10-12 membered bicyclic heterocycle having one, two or three heteroatoms independently selected from the group consisting of N, O, and S;

$R^{41}$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, cyano, nitro, alkoxy, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, oxo, $C_{3-6}$cycloalkyl, heterocyclyl, heteroaryl and phenyl;

$R^{42}$ is independently selected, for each occurrence, from the group consisting of halogen, hydroxyl, amino, amido, sulfonyl, sulfonamide, thiol, $C_{1-6}$alkyl, halo$C_{1-6}$alkyl, carboxyl, cyano, nitro, alkoxy, —C(O)O—$C_{1-6}$alkyl, —OC(O)O—$C_{1-6}$alkyl, —OC(O)NR'R', —N(R')C(O)NR'R', —N(R')C(O)O—$C_{1-6}$alkyl, oxo, $C_{3-6}$cycloalkyl, heterocyclyl, heteroaryl and phenyl;

R' is independently selected, for each occurrence, from the group consisting of hydrogen or $C_{1-6}$alkyl; wherein $C_{1-6}$alkyl is optionally substituted with one, two, three or more substituents each selected from $R^{42}$;

or two R' may be taken together with the nitrogen to which they are attached to form a saturated, partially saturated or unsaturated, 4-7 membered monocyclic or 10-15 membered bicyclic heterocycle having one, two or three heteroatoms independently selected from the group consisting of N, O, and S;

or a R' substituent and a $R^2$, $R^3$, $R^4$ or $R^5$ substituent may be taken together with the atoms to which they are attached to form a saturated, partially saturated or unsaturated, 4-6 membered monocyclic or 10-12 membered bicyclic heterocycle having one, two or three heteroatoms independently selected from the group consisting of N, O, and S;

n is selected from the group consisting of 0, 1, 2, 3 and 4;

p is selected from the group consisting of 0, 1, 2, 3 and 4;

m is selected from the group consisting of 0, 1, or 2; or pharmaceutically acceptable salts or stereoisomers thereof.

In one embodiment, A¹ and A² may be independently selected from the group consisting of O—$C_{3-6}$cycloalkyl, —NR'—$C_{3-6}$cycloalkyl, —S—$C_{3-6}$cycloalkyl, —O-heterocyclyl, —NR'-heterocyclyl, —S-heterocyclyl, —O-phenyl, —O-naphthyl, —NR'-phenyl, —NR'-naphthyl, —S-phenyl, —S-naphthyl, —O-heteroaryl, —NR'-heteroaryl, and —S-heteroaryl.

In a further aspect, a heterocyclic compound is provided, wherein the heterocyclic compound is selected from the group consisting of:

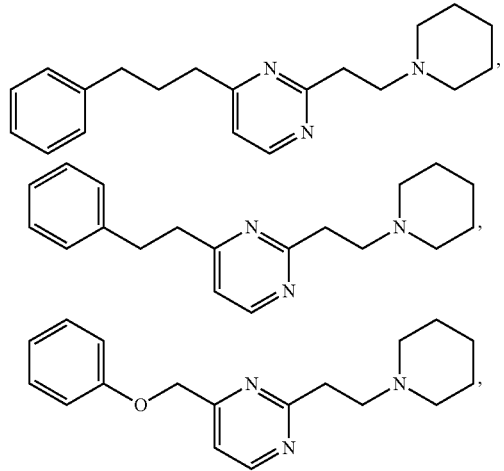

-continued

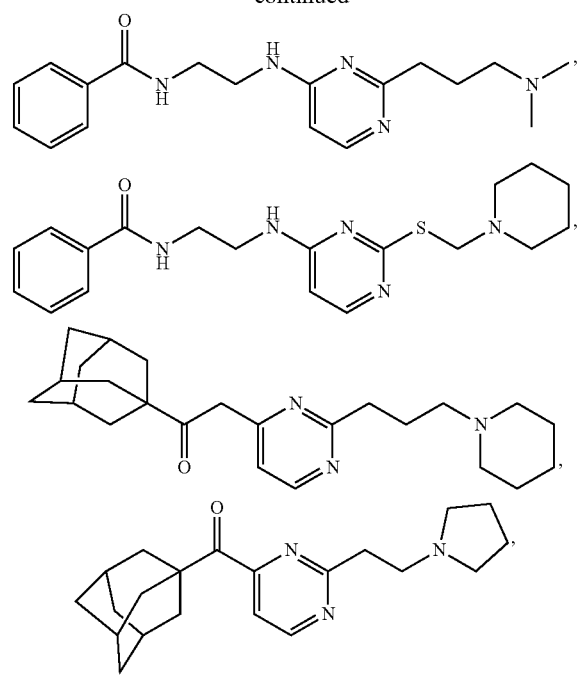

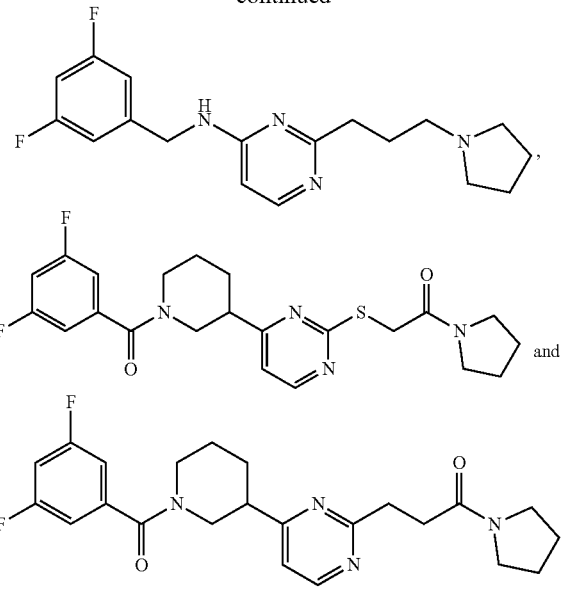

or pharmaceutically acceptable salts thereof.

In another aspect, a heterocyclic compound is provided, wherein the heterocyclic compound is selected from the group consisting of:

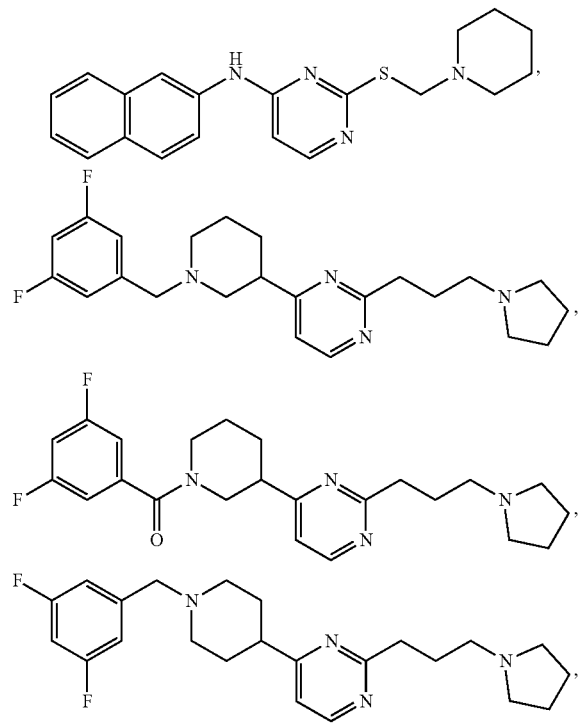

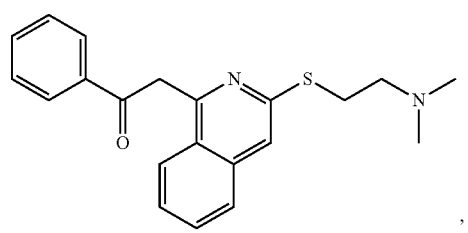

or pharmaceutically acceptable salts thereof.

In an aspect, a heterocyclic compound is provided, wherein the heterocyclic compound is selected from the group consisting of:

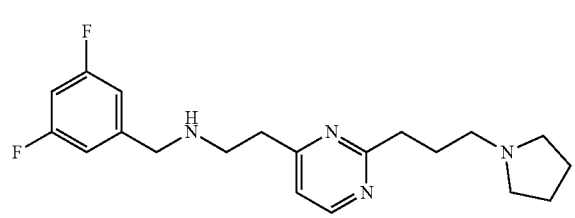

21

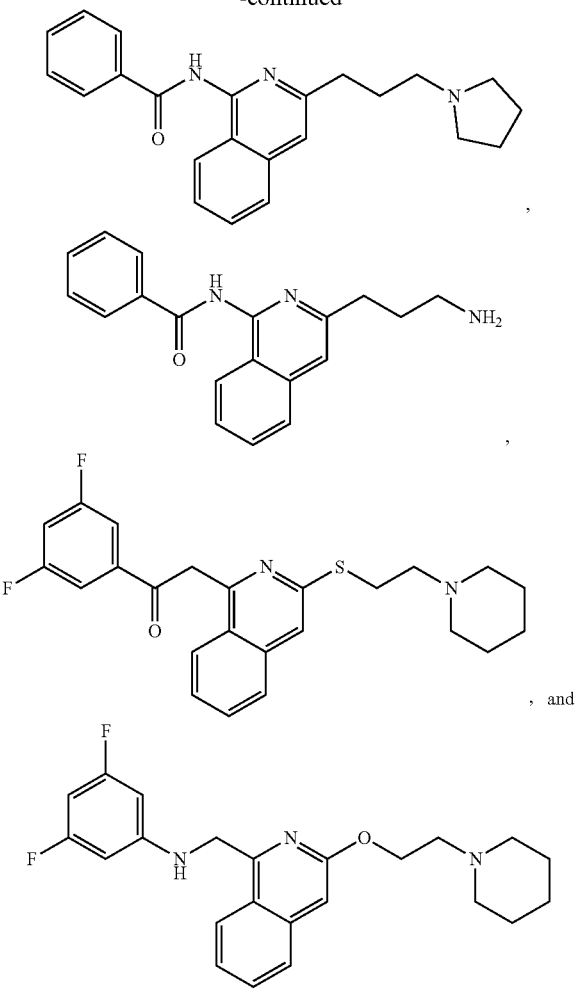

or pharmaceutically acceptable salts thereof.

22

Procedures for making compounds described herein are provided below. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 2nd Ed. (1999)). The deprotection step may be the final step in the synthesis such that the removal of protecting groups affords compounds of Formula I, as disclosed herein. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Multiple methods for preparing compounds described herein are provided in the examples. Further synthetic methods for preparing various compounds described herein are provided by the following schemes. The schemes are given for the purpose of illustrating the invention, but not for limiting the scope or spirit of the invention. Starting materials shown in the schemes can be obtained from commercial sources or can be prepared based on procedures described in the literature.

The synthetic route in Scheme 1 illustrates a general method for preparing pyrimidine derivatives, including bicyclic derivatives. The method involves attaching the desired substituents to the pyrimidine core. The desired nucleophile group can be installed at either the 2-position or 4-position of the pyrimidine core by reacting dihalopyrimidine A with the appropriate nucleophile to provide either B1 or B2. The reactivity will be dependent on both the nucleophile and the halogens on A, which provides the opportunity to afford either B1 or B2. The alkyne group can be installed by reacting B1 or B2 with the appropriate alkyne, utilizing Sonogashira reaction conditions. The Sonogashira product $C_1$ or $C_2$ can be reduced to provide final product D1 or D2.

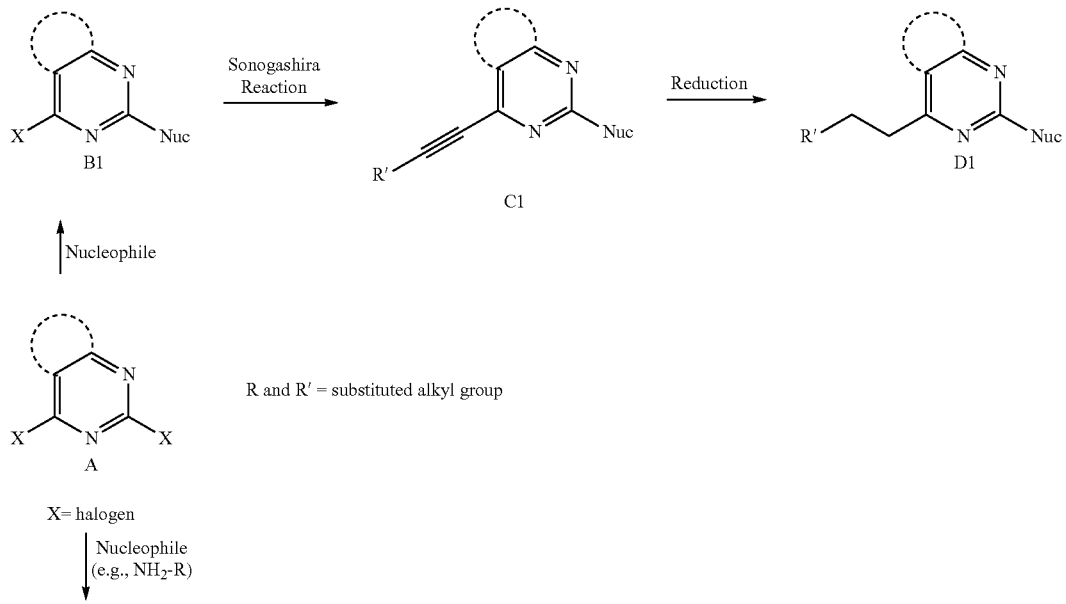

SCHEME 1

-continued

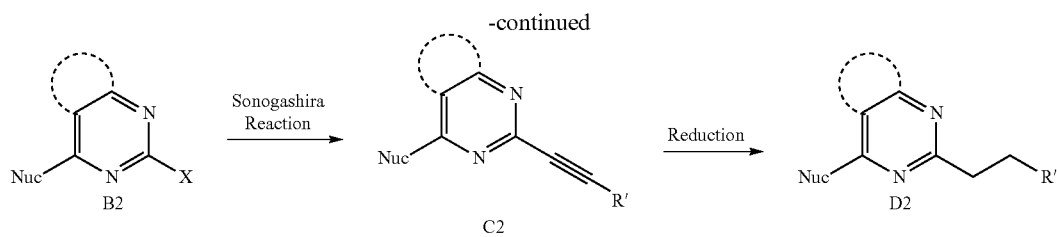

Scheme 2 provides an additional exemplary method for preparing pyrimidine derivatives, including bicyclic derivatives. Similar to Scheme 1, the method involves attaching the desired substituents to the pyrimidine core. The alkyne group can be installed by reacting A with the appropriate alkyne, utilizing Sonogashira reaction conditions. The Sonogashira product B can be reduced to provide alkyl pyrimidine C. Deprotonation of C with LDA and reaction with the appropriate electrophile (e.g., acyl chlorides) affords the final disubstituted pyrimidine D.

SCHEME 2

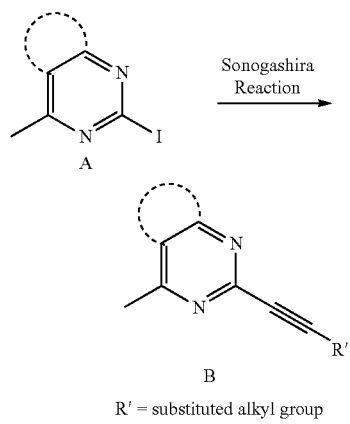

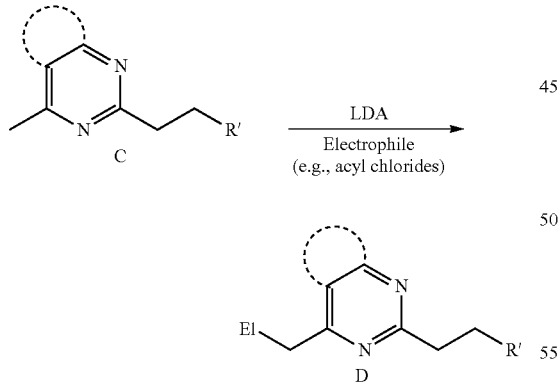

Scheme 3 provides a more detailed exemplary synthetic procedure for making pyrimidine derivatives having various functional groups (e.g., alkylamino or acyl groups) at the C2- and C4-position of the pyrimidine ring. The acyl group can be installed by reacting acid chloride A with the appropriate zinc bromide substrate. The alkene product C can be provided by utilizing the Stille reaction. Reaction of alkene C with the desired amino group affords the final disubstituted pyrimidine D.

SCHEME 3

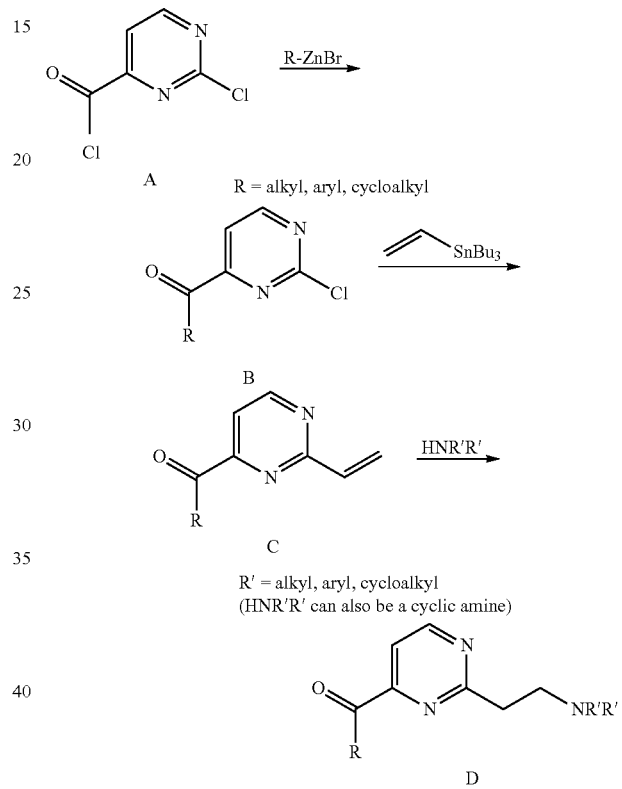

Scheme 4 provides an alternative approach to making pyrimidine or pyridine derivatives, including bicyclic derivatives, having various functional groups. Deprotonation of A with LDA and reaction with the appropriate electrophile (e.g., Weinreb Amide or benzyl bromide) affords the alkyl substituted pyrimidine B. The alkene product C can be provided by utilizing the Stille reaction. Reaction of alkene C with the desired amino group affords the final disubstituted heterocycle D.

SCHEME 4

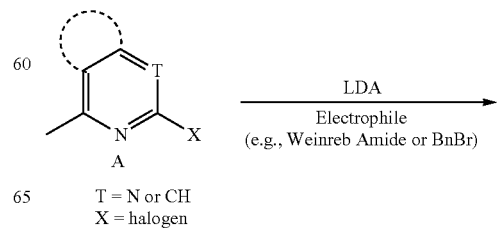

T = N or CH
X = halogen

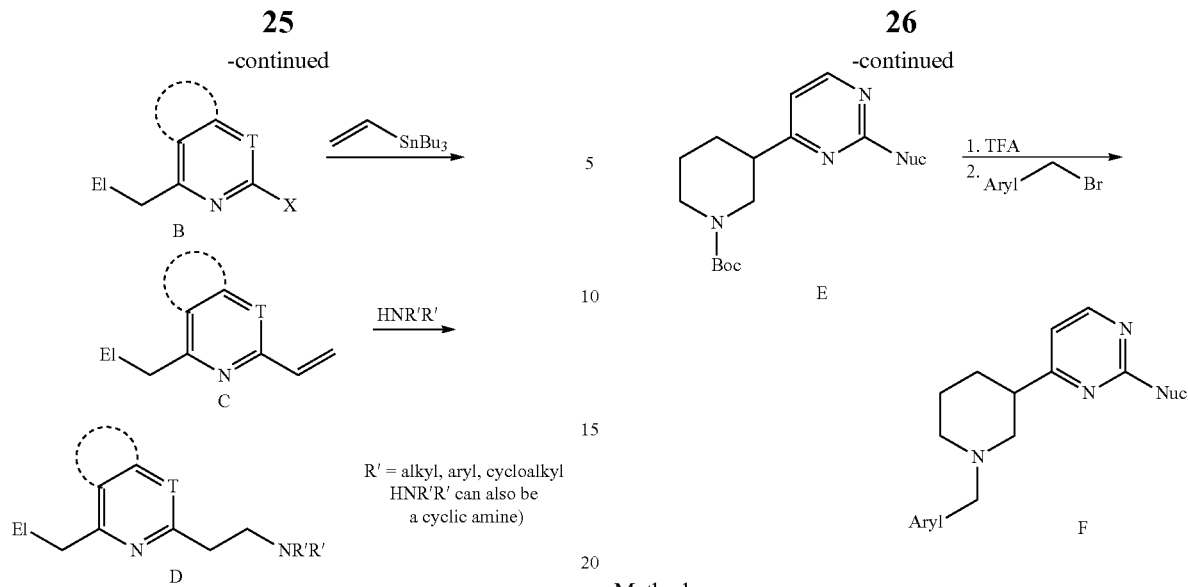

Scheme 3 provides a more detailed exemplary synthetic procedure for making pyrimidine derivatives having various functional groups (e.g., cyclic amino groups) at the C4-position of the pyrimidine ring. The acid B can be provided by reacting cyclic amine A with di-tert-butyl dicarbonate followed by saponification. Condensation with N-methyl-N-methoxy amine followed by reaction with methyl magnesium bromide can provide ketone C. The pyrimidine intermediate D can be installed by reacting C with Bredereck's reagent followed by reaction with guanidine. The Sandmeyer reaction can be utilized to provide the chloro-derivative of pyrimidine intermediate D. The desired nucleophile can be installed by reaction of the chloro-derivative of D with the appropriate nucleophile to afford E. The cyclic amine can be substituted with the appropriate aryl group, following deprotection of the boc-group, to afford the final disubstituted pyrimidine F.

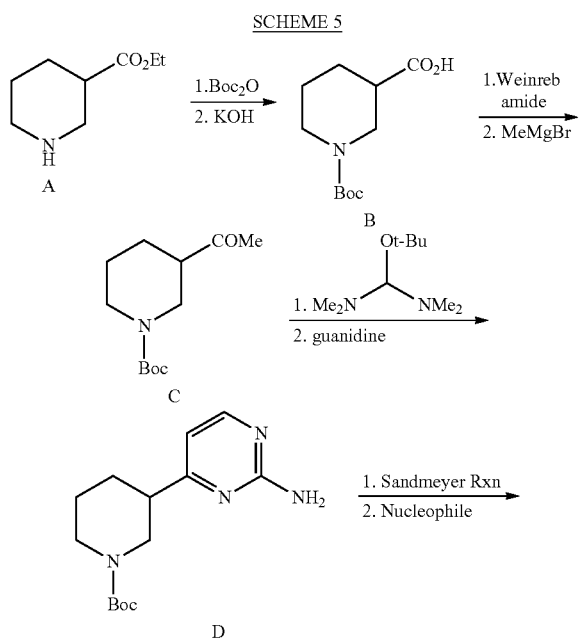

Methods

One aspect of the disclosure provides methods of modulating the activity of T cell receptors, comprising administering a pharmaceutically effective amount of a disclosed heterocyclic compound to a patient in need thereof. In some embodiments, the compound utilized by one or more of the foregoing methods is one of the generic, subgeneric, or specific compounds described herein, such as a compound of Formula I, IA, IB, IC, ID, IE, IF, IG, IH, or II. The ability of compounds described herein to modulate or inhibit T cell receptors can be evaluated by procedures known in the art and/or described herein. Another aspect of the disclosure provides methods of treating a disease associated with expression or activity of T cell receptor, comprising administering a pharmaceutically effective amount of a disclosed heterocyclic compound, such as a compound of Formula I, IA, IB, IC, ID, IE, IF, IG, IH, or II, to a patient in need thereof.

In certain embodiments, the invention provides a method of treating a disease or disorder selected from the group of acute and chronic immune inflammatory disorders, e.g., Crohn's disease, ulcerative colitis, rheumatic disorders, psoriasis, and allergies, comprising administering a pharmaceutically effective amount of a disclosed heterocyclic compound, e.g. a compound of Formula I, IA, IB, IC, ID, IE, IF, IG, IH, or II, to a patient in need thereof.

Methods of treating gastrointestinal diseases are provided, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating inflammatory bowel diseases, e.g., ulcerative colitis, Crohn's disease, indeterminate colitis; and diverticulitis.

Also provided herein are methods of treating endocrine disorders, comprising administering a pharmaceutically effective amount of a disclosed heterocyclic compound, e.g. a compound of Formula I, IA, IB, IC, ID, IE, IF, IG, IH, or II, to a patient in need thereof. For example; congenital adrenal hyperplasia; hypercalcemia associated with cancer; and nonsuppurative thyroiditis are provided.

Methods of treating rheumatic disorders are provided, comprising administering a pharmaceutically effective amount of a disclosed heterocyclic compound, e.g. a compound of Formula I, IA, IB, IC, ID, IE, IF, IG, IH, or II, to a patient in need thereof. For example, contemplated methods include methods of treating psoriatic arthritis; rheumatoid arthritis, including juvenile rheumatoid arthritis; ankylosing spondylitis; acute and subacute bursitis; acute nonspecific tenosynovitis; acute gouty arthritis; post-traumatic osteoarthritis; synovitis of osteoarthritis; and Epicondylitis. For example, the treatment may comprise an adjunctive therapy for short-term administration, wherein the patient in need thereof is having an acute episode or an exacerbation. In another example, selected methods, for example methods of treating rheumatoid arthritis, may require low-dose maintenance therapy.

Provided herein are methods of treating collagen diseases, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating systemic lupus erythematosus; systemic-dermatomyositis (e.g., polymyositis); and acute rheumatic carditis. For example, the treatment may be administered as maintenance therapy and/or when the patient in need thereof is having an acute episode or an exacerbation.

Also provided herein are methods of treating dermatologic diseases, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating pemphigus; bullous dermatitis herpetiformis; erythema multiforme, e.g., Stevens-Johnson syndrome; exfoliative dermatitis; mycosis fungoides; psoriasis; and seborrheic dermatitis.

Methods of treating allergic conditions are provided, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating seasonal or perennial allergic rhinitis; bronchial asthma; contact dermatitis; atopic dermatitis; serum sickness; and drug hypersensitivity reactions. For example, these methods include control of severe or incapacitating allergic conditions that are hard to control with conventional treatment.

Provided herein are methods of treating ophthalmic diseases, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating acute and chronic allergic and inflammatory processes involving the eye and/or its adnexa such as: allergic cornea marginal ulcers; herpes zoster ophthalmicus; anterior segment inflammation; uveitis, scleritis, episcleritis and choroiditis; sympathetic ophthalmia; allergic conjunctivitis; keratitis; chorioretinitis; optic neuritis; iritis and iridocyclitis.

Methods of treating respiratory diseases are provided, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating symptomatic sarcoidosis; Loeffler's syndrome; berylliosis; fulminating or disseminated pulmonary tuberculosis, for example, wherein the treatment can comprise of concurrent administration of a disclosed compound and an appropriate antituberculous chemotherapy; and aspiration pneumonitis.

Also provided herein are methods of treating hematologic diseases, comprising administering a pharmaceutically effective amount of a disclosed heterocyclic compound, e.g. a compound of Formula I, IA, IB, IC, ID, IE, IF, IG, IH, or II, to a patient in need thereof. For example, contemplated methods include methods of treating idiopathic thrombocytopenic purpura; secondary thrombocytopenia; acquired (autoimmune) hemolytic anemia; erythroblastopenia (RBC anemia); and congenital (erythroid) hypoplastic anemia.

Provided herein are methods of treating neoplastic diseases, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating leukemia and lymphoma, including a method of treating acute leukemia in children.

Also provided herein are methods of treating edematous states, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of inducing diuresis or remission of proteinuria in the nephrotic syndrome, without uremia, of the idiopathic type or that due to lupus erythematosus.

Provided herein are methods of treating nervous system diseases and/or disorders, comprising administering a pharmaceutically effective amount of a disclosed heterocyclic compound, e.g. a compound of Formula I, IA, IB, IC, ID, IE, IF, IG, IH, or II, to a patient in need thereof. Contemplated methods include, for example, methods of treating multiple sclerosis.

Also provided herein are methods of treating tuberculous meningitis with subarachnoid block or impending block, comprising administering a pharmaceutically effective amount of a disclosed heterocyclic compound, e.g. a compound of Formula I, IA, IB, IC, ID, IE, IF, IG, IH, or II, used concurrently with appropriate antituberculous chemotherapy, to a patient in need thereof; and methods of treating trichinosis with neurologic or myocardial involvement, comprising administering a pharmaceutically effective amount of a disclosed heterocyclic compound, e.g. a compound of Formula I, IA, IB, IC, ID, IE, IF, IG, IH, or II, to a patient in need thereof.

In some embodiments, provided here are compounds that bind to and/or modulate the glucocorticoid receptor. For example, provided herein is a method of identifying a glucocorticoid receptor modulator, comprising: providing isolated peripheral blood lymphocytic cells; contacting the cells with phytohaemagglutinin to prepare stimulated cells; contacting a proposed glucocorticoid receptor modulator with the stimulated cells; and measuring the activity of the proposed glucocorticoid receptor modulator to identify modulation activity.

Pharmaceutical Compositions and Administration

The disclosure provides pharmaceutical compositions, which comprise a therapeutically-effective amount of one or more of the compounds described above, formulated together with one or more pharmaceutically acceptable carriers (additives) and/or diluents. The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally; or other formulations to be used as aerosols and/or nebulizers.

In one embodiment, the pharmaceutical compositions of the present disclosure may be administered orally. However, the pharmaceutical compositions may be administered parenterally, by inhalation spray, topically, rectally, nasally, buccally, vaginally or via an implanted reservoir. Contemplated non-parenteral administration includes oral, buccal, transdermal (e.g., by a dermal patch), topical, inhalation, or sublingual administration, or, e.g., ocular, pulmonary, nasal, rectal or vaginal administration. For example, a contemplated pharmaceutical compositions may be administered orally, intraperitoneally or intravenously.

Sterile injectable forms of the pharmaceutical compositions may be aqueous or oleaginous suspensions. These suspensions may be formulated according to techniques known in the art, using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers, which are commonly used in the manufacture of pharmaceutically acceptable solid, liquid, or other dosage forms may also be used for the purposes of formulation.

The pharmaceutical compositions of this disclosure may be orally administered in any orally acceptable dosage form including, but not limited to, solid forms such as capsules, tablets, pills, powders, and granules, which may be prepared using any suitable process known to the art. For example, a disclosed compound may be mixed with enteric materials and compressed into tablets. In the case of tablets for oral use, carriers commonly used include microcrystalline cellulose, lactose and corn starch. Lubricating agents, such as magnesium stearate, are also typically added.

Alternatively, formulations of the disclosure may be incorporated into chewable tablets, crushable tablets, tablets that dissolve rapidly within the mouth, or mouth wash.

Liquid dosage forms for oral or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents. If desired, certain sweetening, flavoring or coloring agents may also be added.

The pharmaceutical compositions of this disclosure may also be administered by nasal aerosol or inhalation. Such pharmaceutical compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

For example, for pulmonary (e.g., intrabronchial) administration, disclosed compounds can be formulated with conventional excipients to prepare an inhalable composition in the form of a fine powder or atomizable liquid. For ocular administration, disclosed compounds can be formulated with conventional excipients, for example, in the form of eye drops or an ocular implant. Among excipients useful in eye drops are viscosifying or gelling agents, to minimize loss by lacrimation through improved retention in the eye.

Should topical or transdermal administration be desired, it can be accomplished using any method commonly known to those skilled in the art. Dosage forms for topical or transdermal administration of an inventive pharmaceutical composition includes but is not limited to ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions for rectal or vaginal administration may be suppositories, which can be prepared by mixing a disclosed compound with suitable non-irritating excipients or carriers such as cocoa butter, polyethylene glycol or a suppository wax which are solid at ambient temperature but liquid at body temperature and therefore melt in the rectum or vaginal cavity and release the active agent(s). Alternatively, contemplated formulations can be administered by release from a lumen of an endoscope after the endoscope has been inserted into a rectum of a subject.

The amount of the disclosed compound that may be combined with the carrier materials to produce a pharmaceutical composition in a single dosage form will vary depending upon the host treated and the particular mode of administration. It should be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician as well as the severity of the particular disease being treated. Despite their variety, accounting for these factors in order to select an appropriate dosage or treatment regimen would require no more than routine experimentation.

Additional agents, i.e., agents other than the disclosed compounds, contemplated herein may be administered separately from the therapeutic agents of the disclosure, as part of a multiple dosage regimen. Alternatively, those agents may be part of a single dosage form, mixed together with the therapeutic agents of the disclosure in a single pharmaceutical composition. If administered as part of a multiple dosage regime, the two active agents may be administered simultaneously, sequentially or within a period of time from one another. The amount of both the therapeutic agent, i.e., a disclosed compound, of the disclosure and the additional therapeutic agent that may be combined with the carrier materials to produce a single dosage form will vary depending upon the host treated and the particular mode of administration as well as on the nature of the therapeutic agent of the disclosure and the additional therapeutic agent.

Contemplated methods may include administration of a composition comprising a disclosed compound, for example, hourly, twice hourly, every three to four hours, daily, twice daily, 1, 2, 3 or 4 times a week, every three to four days, every week, or once every two weeks depending on half-life and clearance rate of the particular composition or inhibitor.

Another aspect provides pharmaceutical compositions which comprise a therapeutically effective amount of one or more of the disclosed compounds, formulated together with one or more other therapeutic agents, for example as part of a combination treatment.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. For example, the treatment period can be at least about one month, or at least about six months, or at least about one year, or indefinitely when treating a metabolic disorder.

EXAMPLES

The disclosure is further illustrated by the following examples. The following examples are provided for illustration purposes only, and are not to be construed as limiting the scope or content of the disclosure in any way.

Example 1: Synthesis of 4-(1-benzylpiperidin-3-yl)-2-(2-(pyrrolidin-1-yl)ethylthio)-pyrimidine (S3.4)

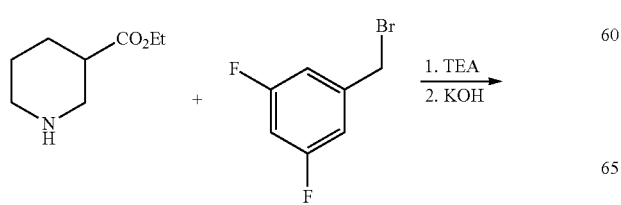

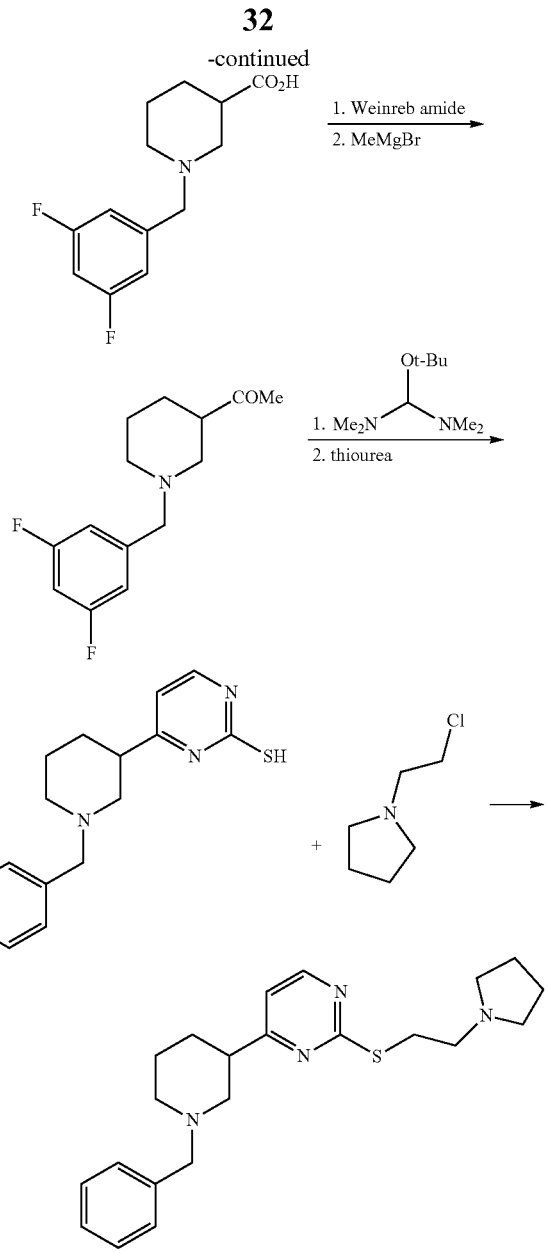

Step 1: 1-(3,5-Difluoro-benzyl)-piperidine-3-carboxylic acid ethyl ester (Intermediate 1)

To a chilled solution (10-15° C.) of ethyl nipecotate (20 g, 0.13 mol) in ethyl acetate (150 g) was added 1-bromomethyl-3,5-difluoro-benzene (28.4 g, 0.14 mol). The mixture was stirred at 10-15° C. for 15 minutes and triethyl amine (14.5 g, 0.14) was added while the reaction temperature was maintained at 10-25° C. (exothermic addition). The resulting white-suspension was stirred at room temperature (20-25° C.) for 16 h.

After the reaction was complete by TLC analysis, water (40 g) was added and the biphasic mixture was stirred for 10 minutes. The organic layer was recovered and poured into another round bottom flask, and the pH was adjusted to 7.5-7.8 by addition of 30% $NH_4OH$ (about 160 g). The organic layer was recovered and the solvent distilled off (vacuum; Tmax: 45° C.) to afford the N-substituted substrate as a brown oil (35.1 g, 95%).

HPLC purity (206 nm): 91.51%
LC/MS [MH]+ found: 284.1, in agreement with the desired compound.

To a solution of the N-substituted substrate (33.4 g, 0.12 mol) in MeOH (200 g) and water (50 g) was added 30% NaOH (32 g, 0.24 mol). The resulting mixture was stirred at 35-40° C. until the reaction was complete by TLC analysis (about 1 h). The solvents were removed by vacuum distillation (T max: 40° C.) to give a solid residue. Water (84 g) was added and the mixture was stirred at 30-35° C. until a clear solution was formed. To the solution was added HCl 32% (44 g, 0.38 mol), leaving the temperature rise to 40° C. The mixture was stirred at 35-40° C. until solid started precipitating out, at which point stirring was continued at 20-25° C. for 1 h. The mixture was cooled at 0-5° C., stirred, filtered and washed with water (30 g). The resulting wet white powder (57 g) was dried into a vacuum oven at 55-60° C. overnight. Intermediate 1 was recovered as a dried white powder (30.7 g, 88%).

LC/MS [MH]+ found: 256.1, in agreement with the desired compound.

residue. Water (60 g) was added to the oil residue and the resulting mixture was stirred at 30-40° C. until a clear solution was formed. To the solution was added HCl 32% (41.4 g, 0.36 mol), resulting in the precipitation of a white solid. The suspension was stirred at 35-40° C. for 1 h, then at 20-25° C. for 1 h and cooled at 0-5° C. and filtered. The solid was washed with water (50 g), and dried in a vacuum oven at 60° C. overnight. The acid substrate was recovered as a white powder (21.8 g, 63.2%).

LC/MS [MH]+ found: 299.1, in agreement with the desired compound.

The acid substrate (20.8 g, 0.062 mol) was suspended in DCM (140 g) and water was added (30 g), followed by NaOH 30% (16.5 g, 0.12 mol). The mixture was stirred at 20-30° C. until the suspended solid was completely dissolved. The organic layer was recovered, washed with water (30 g), 20% NaCl (30 g) and finally distilled under vacuum (T max 45° C.) to afford a brown oily residue (free base). The free base substrate was dissolved in THF (40 g) under a stream of $N_2$ and cooled to 15-20° C. A solution of MeMgBr (12% in THF, 100 g, 0.1 mol) was slowly added, maintaining the temperature at 15-25° C. (exothermic addition). The resulting white-cloudy mixture was stirred at 20-25° C. until the conversion was complete by TLC analysis (ca. 1 h). The reaction was cooled at 10-15° C. and water was slowly added maintaining 10-25° C. (exothermic addition). After stirring, ethyl acetate (100 g) was added, and the organic layer was separated, washed with brine (25 g) and evaporated under vacuum (T max: 46° C.) to afford Intermediate 2 as a clear-orange oil (17.5 g, quantitative recovery).

LC/MS [MH]+ found: 254.1, in agreement with the desired compound.

Step 2: 1-[1-(3,5-Difluro-benzyl)-piperidin-3-yl]-ethanone (Intermediate 2)

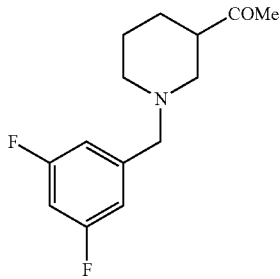

To a suspension of intermediate 1 (30 g, 0.1 mol) in DCM (300 g) was added a catalytic amount of DMF (3 g), and the resulting mixture was heated at reflux (35-42° C.). Thionyl chloride (18.4 g, 0.16 mol) was added and the mixture was stirred until the conversion to the acyl chloride was complete by TLC analysis (about 1.5 h). The solvents were removed by vacuum distillation (T max: 50° C.) to give a crude oil, which was dissolved in DCM (50 g) and distilled again under vacuum.

To the resulting crude residue in DCM (270 g) was added N-methoxy-N-methylamine HCl (11.7 g, 0.12 mol) and triethyl amine (33.4 g, 0.33 mol). The obtained suspension was stirred at 20-25° C. for 17 h. The mixture was diluted with DCM (150 g); water (80 g) was added and the organic layer was separated. The organic layer was washed twice with 5% $NaHCO_3$ (80 g×2) and distilled to give an oil Step 3: 4-[1-(3,5-Difluro-benzyl)-piperidin-3-yl]-pyrimidine-2-thiol (Intermediate 3)

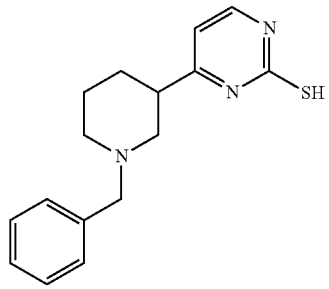

To a solution of intermediate 2 (16.5 g, 0.065 mol) in DMF (33 g) was added DMF-DMA (15.5 g, 0.13 mol). The resulting clear solution was stirred under vigorous reflux (T oil bath: 140° C., T solution: 115-120° C.). Stirring and heating was continued for ca. 1.5 and then the reaction was allowed to stir at room temperature overnight (16 h). The solvents were removed by vacuum distillation (T max: 100° C.), and the resulting dark-oil was dissolved in toluene (80 g), washed with water (40 g), brine (20 g) and evaporated under vacuum (T max: 70° C.). The resulting residue was dissolved in DMF (20 g), and DMF-DMA was added (15.5 g, 0.13 mol). The reaction was heated at reflux for 10 h. After another addition of DMF-DMA (5 g, 0.042 mol), the mixture was heated for a further 4 h (complete conversion by TLC).

The reaction was cooled to room temperature, diluted with toluene (100 g), washed with water (50 g) and bring (30 g×2). The recovered organic layer was evaporated by vacuum distillation (T max: 80° C.) to afford the α,β-unsaturated substrate as a dark-oil, which was used for the next step without further purification.

LC/MS [MH]+ found: 309.1, in agreement with the desired compound.

To a heated solution 30-35° C. of α,β-unsaturated substrate (0.065 mol) in absolute EtOH (50 g) was added EtONa (5.3 g, 0.078 mol), followed by thiourea (5.4 g, 0.072 mol). The resulting dark-red mixture was stirred at 65-70° C. until TLC analysis showed complete conversion (4 h). The solvent was evaporated by vacuum distillation (T max: 50° C.) to give a crude oily residue, which was successively dissolved in acetone (30 g) at 35-40° C. HCl 32% (5 g, 0.13 mol) was added and the solution was stirred at 35-40° C. for 15 min, then cooled at 20-25° C. for 30 min. Since no precipitation was observed, the solvents were removed by vacuum distillation (T max: 50° C.) to provide a residue. Water (40 g) was added, and the resulting mixture was stirred at 20-25° C. for 15 min, then cooled at 5-10° C. and stirred until precipitation occurred. The solid was filtered at 5-10° C. and was washed with cooled water (10 g; 5-10° C.) and cooled acetone (10 g; 5-10° C.). The wet powder recovered (11 g) was dried into a vacuum oven at 50° C. overnight to afford Intermediate 3 as a yellow powder (9 g, 39%).

LC/MS [MH]+ found: 322.1, in agreement with the desired compound.

To a suspension of intermediate 3 (8.5 g, 0.024 mol) in EtOH (40 g) and THF (5 g) was added Na$_2$CO$_3$ (7.9 g, 0.074 mol) followed by 1-(2-chloro-ethyl)-pyrrolidine hydrochloride (4.3 g, 0.025 mol). The resulting mixture was stirred at 55-60° C. for 1.5 h (reaction complete by TLC). The reaction was concentrated by vacuum distillation at 50° C., then cooled at 20-25° C. and diluted with ethyl acetate (60 g). Water was added, and the organic layer was separated, washed with water (20 g) and brine (10 g) and then evaporated under reduce pressure (T max: 50° C.) to give an oily residue (11 g). This oil was dissolved in acetone (30 g) at 45-50° C., then aqueous 32% HCl (8.4 g, 0.073 mol) was added. The solvents were evaporated under vacuum at 70° C., providing a dark-red oil. Acetone (40 g) was added and the mixture was stirred at reflux until precipitation occurred. The resulting suspension was successively cooled at 20-25° C. and stirred for 1 h, then cooled at 8-13° C. and stirred for 30 min. The suspension was filtered under suction, and the solid was washed with cooled acetone (10 g; 5-10° C.). The wet yellow-powder recovered (7.8 g) was divided into two parts: 0.8 g were dried in a ventilated oven at 70° C. for 16 h, providing the hydrochloride salt of the title compound (0.5 g), which was stored for analytical evaluation.

HPLC purity (206 nm): 99.40%.

LC/MS [MH]+ found: 419.1, in agreement with the desired compound.

The remaining portion of the hydrochloride salt (about 7 g) was suspended in DCM (70 g) and neutralized by the addition of 30% NH$_4$OH (10 g, 0.043 mol). After stirring at 20-25° C., the organic layer was separated, washed with water and brine and evaporated under reduced pressure at 50° C. to afford a brown oil, which was further concentrated under vacuum overnight. The oil was dissolved in ethyl acetate (40 g) and evaporated under reduced pressure at 55-60° C. The resulting brown oil was further dried under reduced pressure at 55-60° C. for 5 h and finally at 20-25° C. overnight. The title compound S3.4 was provided as a brown oil (5.1 g, 47%).

HPLC purity (206 nm): 99.01%

LC/MS [MH]+ found: 419.1, in agreement with the desired compound.

Step 4: 4-(1-benzylpiperidin-3-yl)-2-(2-(pyrrolidin-1-yl)ethylthio)pyrimidine (S3.4)

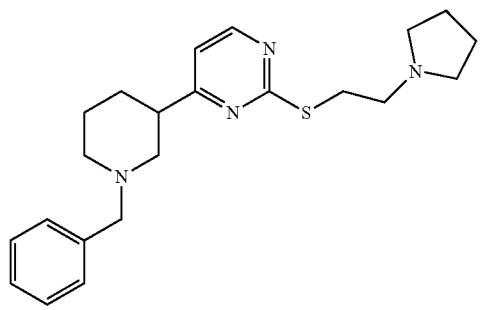

S3.4

Example 2

The compound is prepared using the following scheme:

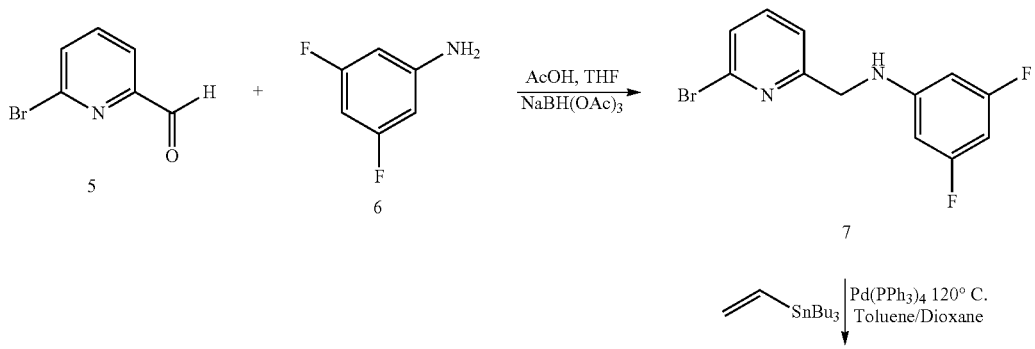

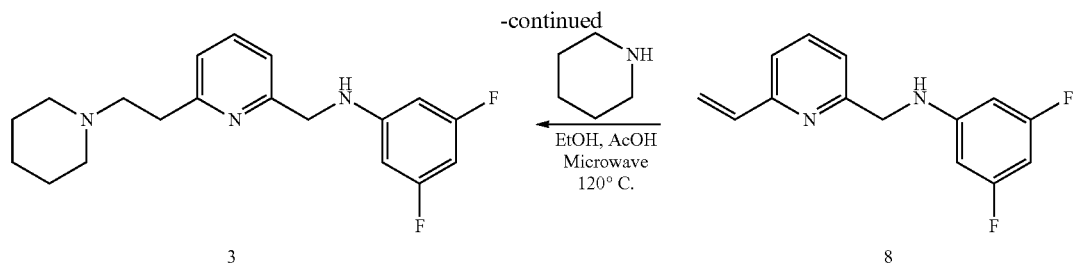
A reductive amination (starting from the commercially available aldehyde 5) was carried out in 49% yield. The Stille reaction allowed the formation of compound 8. This was followed by the addition of piperidine under microwave conditions to afford the final product in good yield.
Example 3
The compound is prepared as follows:
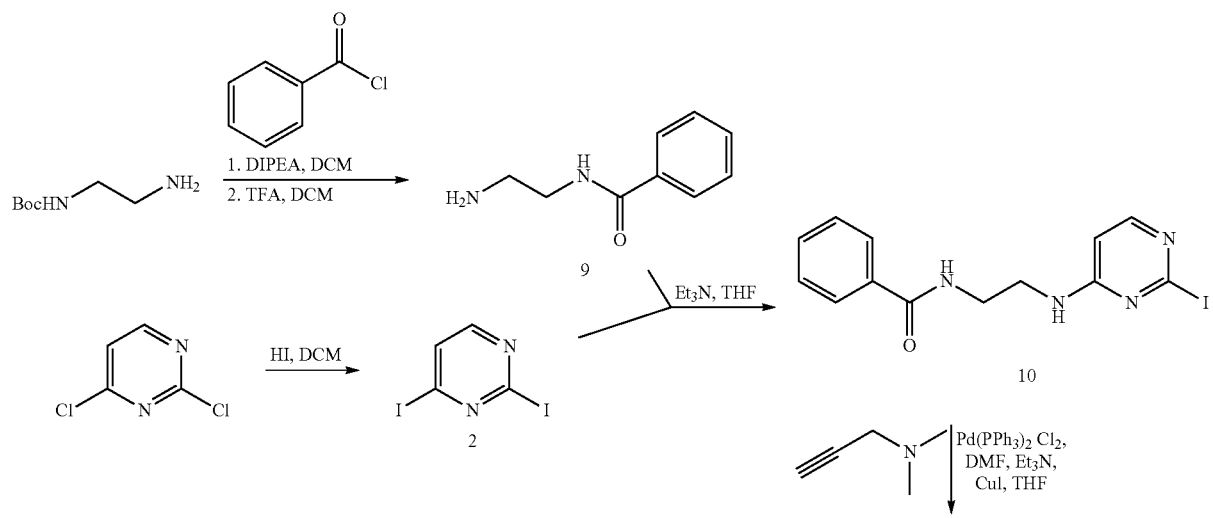

The side chain was prepared in a first approach before introduction on the pyrimidine core. Compound 9 was prepared in a two step process from easily obtainable starting material. A SNAr reaction gave the introduction at position 4 (compound 10) and 2. These two compounds could be separated on silica. A Sonogashira reaction was then carried out to give 11 in good yield. The final hydrogenation gave the desired product without major difficulties.

Example 4

The compound is prepared as follows:

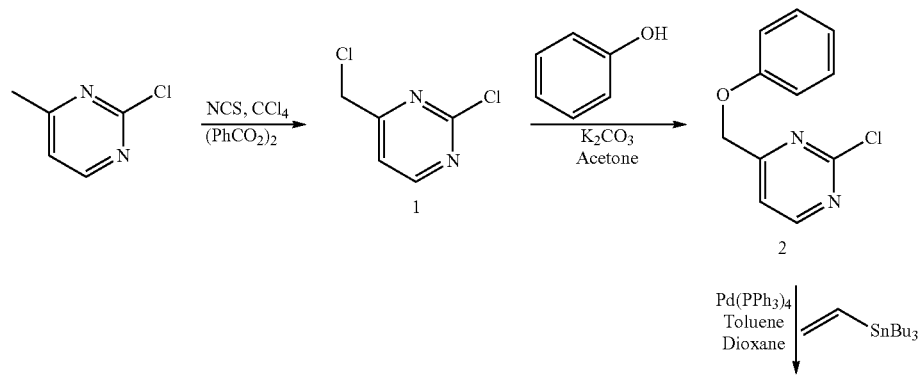

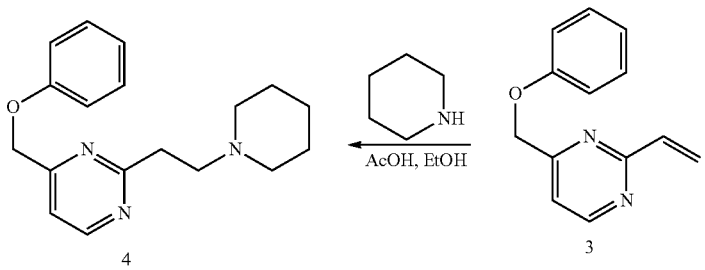

The synthetic route to obtain compound 4 started from a chloration of 4-methyl-2-chloropyrimidine. Compound 1 was obtained in 28% yield after purification. The SNAr reactionwas carried out in 52% yield. The Stille reaction was then realised. The product 3 was obtained in 72% yield. The introduction of piperidine was then carried out under microwave conditions. After purification, the final product was obtained in 19% yield.

Example 5

The compound is prepared as follows:

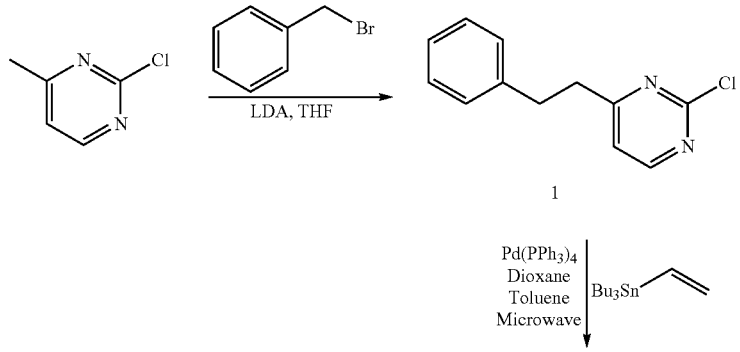

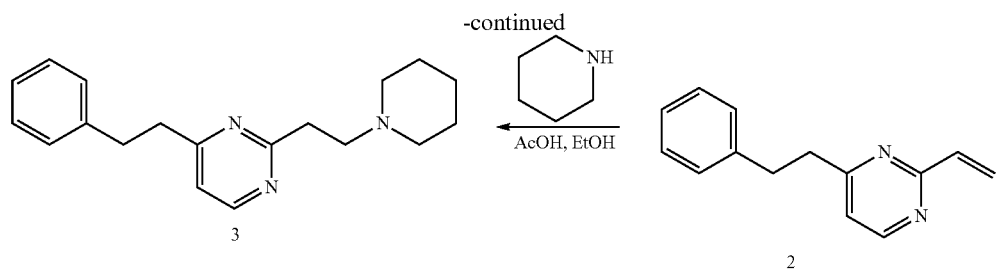

The deprotonation/alkylation of 4-methyl-2chloro-pyrimidine allowed the synthesis of intermediate 1 in 27% yield. The Stille reaction gave the desired product 2 in 51% yield after purification. Compound 2 was engaged in the introduction of piperidine to give the final product 3. The final product was obtained in 49% yield after purification.

Example 6

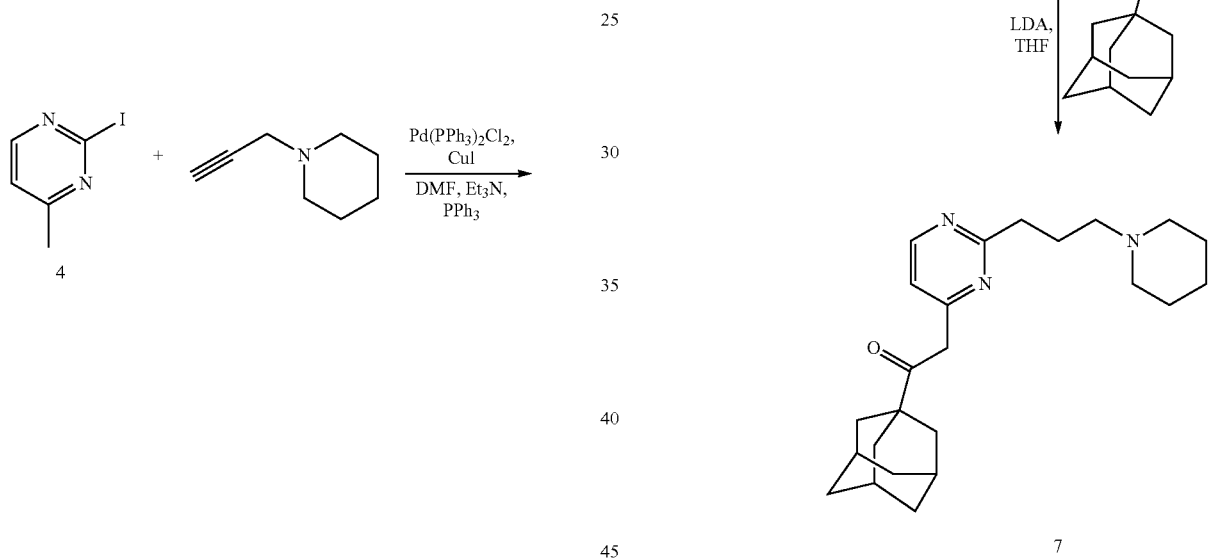

Starting from 4-methyl-2-pyrimidine, a Sonogashira was realised in good yield. This was followed by hydrogenation of the alkyne to give 6 in 33% yield. A deprotonation/alkylation led to the formation of compound 7. After purification, the NMR was complex. A mixture of 2 products after purification were obtained. NMRs in MeOD and DMSO appear to confirm that the product exist as an exchangeable mixture of enol and ketone.

Example 7

Compounds listed in Table 1 below were prepared using procedures analogous to those described herein. Spectral data is shown in FIGS. 8A, 8B, 8C, 8D, 8E, and 8F.

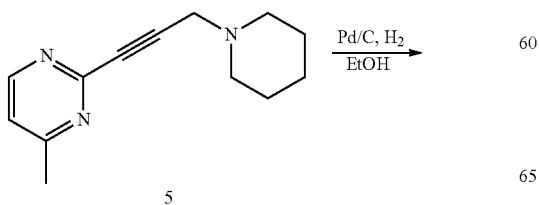

| Example No. | Compound Structure | MS Calc. M⁺ | MS Found M⁺ + 1 | Retention Time |
|---|---|---|---|---|
| 1 | 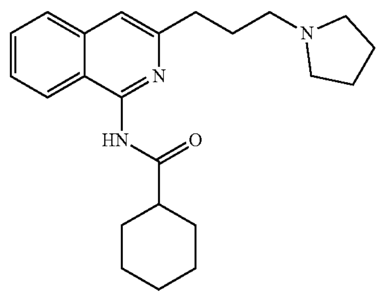 [SMILES: O=C(Nc1nc(CCCN2CCCC2)cc2ccccc12)C1CCCCC1] | 365.52 | 366.2 | 2.80 min |
| 2 | 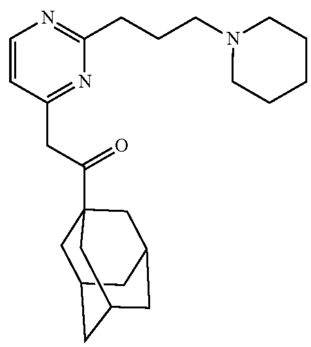 [SMILES: O=C(Cc1ccnc(CCCN2CCCCC2)n1)C12CC3CC(CC(C3)C1)C2] | 418.56 | 419.2 | 2.12 min |
| 3 | 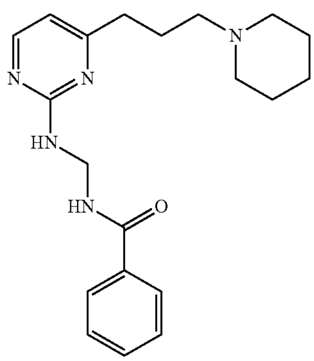 [SMILES: O=C(NCNc1nccc(CCCN2CCCCC2)n1)c1ccccc1] | 367.50 | 368.2 | 1.46 min |
| 4 | 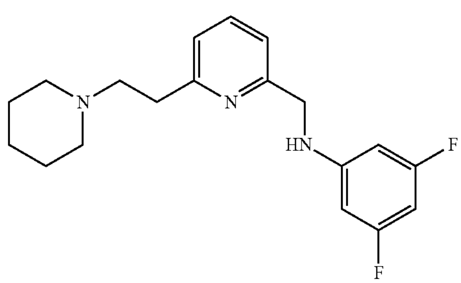 [SMILES: Fc1cc(F)cc(NCc2cccc(CCN3CCCCC3)n2)c1] | 331.41 | 332.2 | 3.31 min |
| 5 | | 295.43 | 296.1 | 3.36 min | compound 4.4

| Example No. | Compound Structure | MS Calc. M+ | MS Found M+ + 1 | Retention Time |
|---|---|---|---|---|
| 6 | 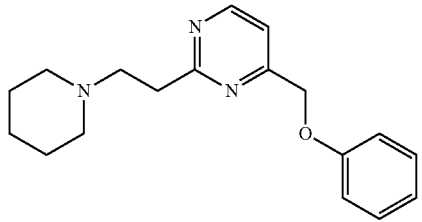 [SMILES: c1ccc(OCc2ccnc(CCN3CCCCC3)n2)cc1] | 297.40 | 298.1 | 3.07 min |
| | 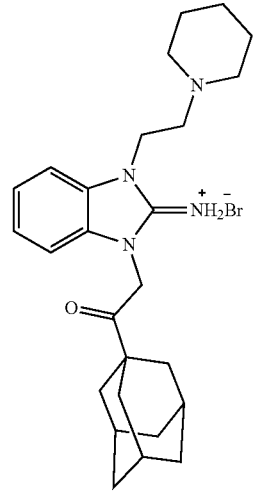 3.1 | | | |
| | 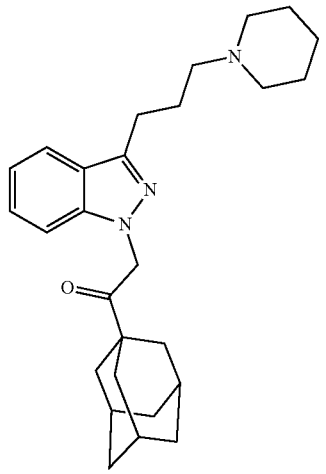 compound 4.1 | | | |

Example 8: Inhibition of T Lymphocyte Proliferation

Select compounds were screened for their ability to inhibit T lymphocyte proliferation.

Human peripheral blood lymphocytes (PBLs) were isolated from whole blood of healthy volunteers by Ficoll-Isopaque density gradient centrifugation. After washing, monocytes were separated from lymphocytes by percoll density gradient centrifugation. The lymphocytes were cultured in IMDM (Gibco, Verviers, Belgium) supplemented with 10% heat inactivated fetal calf serum.

Cells were seeded in 96 well plates and stimulated with PHA (10 µg/ml) and corresponding concentration of pharmaceuticals. After 24 hours tritiated thymidine was added to each well and left overnight. Next morning proliferation was measured by microbeta counter. Graphs were plotted with the untreated condition set to a hundred percent.

Figure 1B:
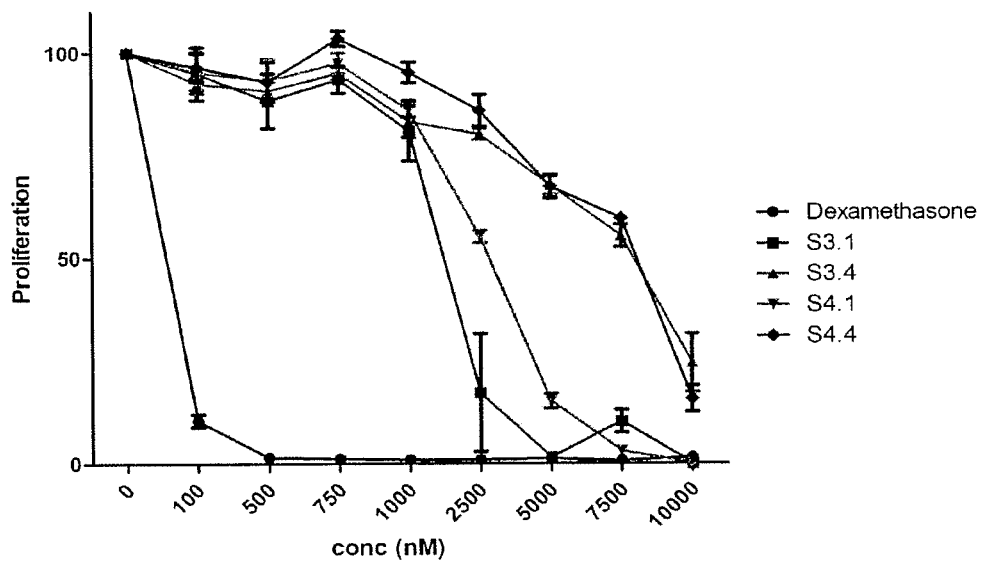

As shown in FIGS. 1A and 1B, the antiproliferative effect of the compounds S3.1, S3.4, S4.1, and S4.4 is compared to glucocorticoids, such as prednisolone, dexamethasone, and hydrocortisone. To test the potential of the compounds, inhibition of proliferation was plotted against known corticosteroids (FIG. 1A). Dexamethasone is the most powerful corticosteroid used in this experiment and also one of the most potent anti-inflammatory drugs known. Prednisolone is a more commonly used corticosteroid and hydrocortisone is the equivalent of the steroids produced in the adrenal cortex.

Figure 1C:
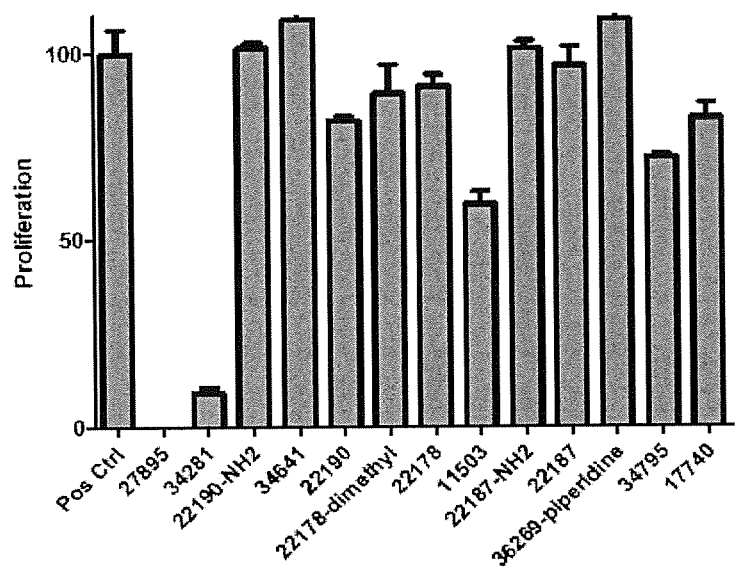
Figure 7:
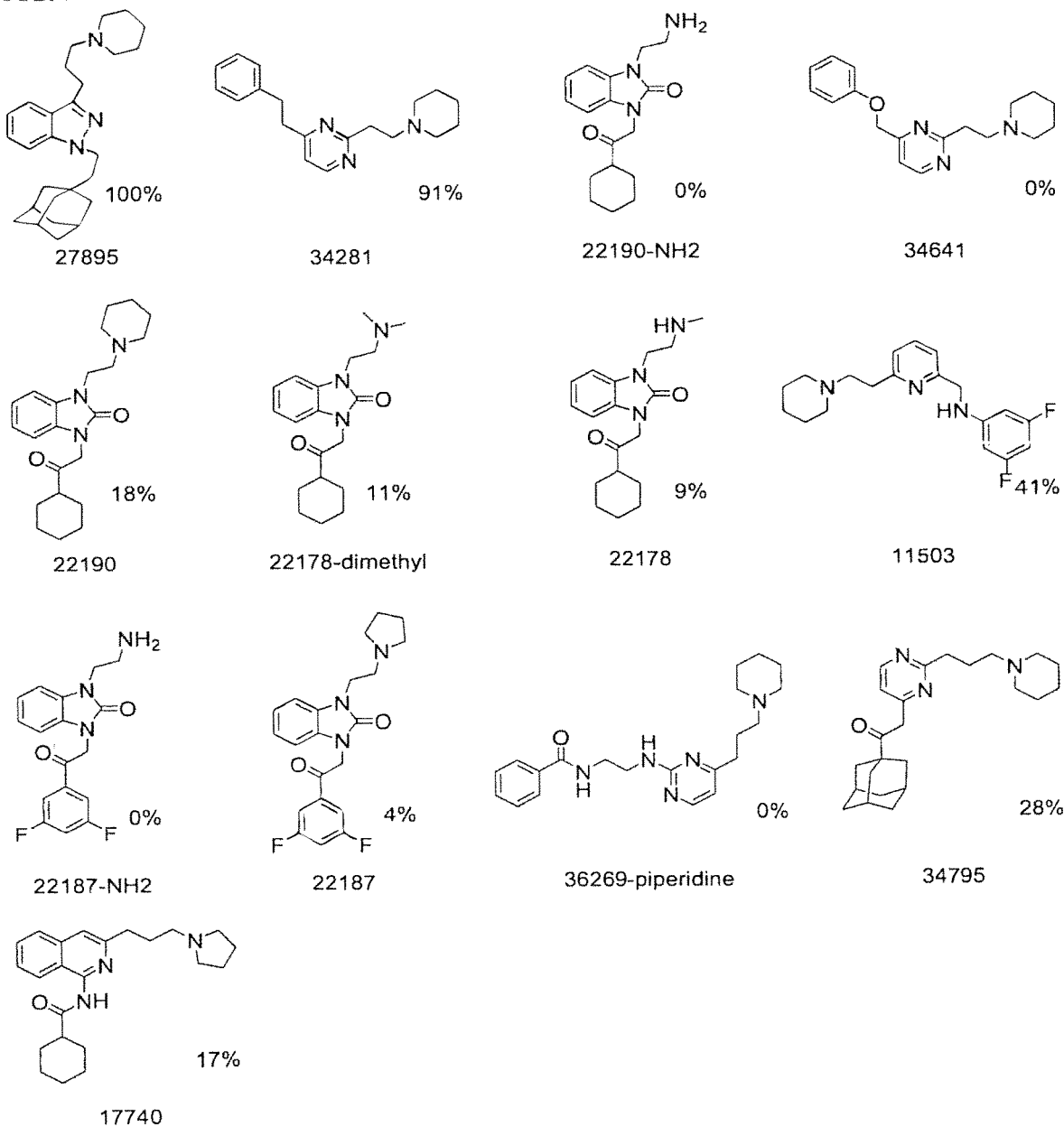
FIG. 7 shows percent inhibition in a lymphocyte proliferation assay for disclosed compounds.
Figure 8A:
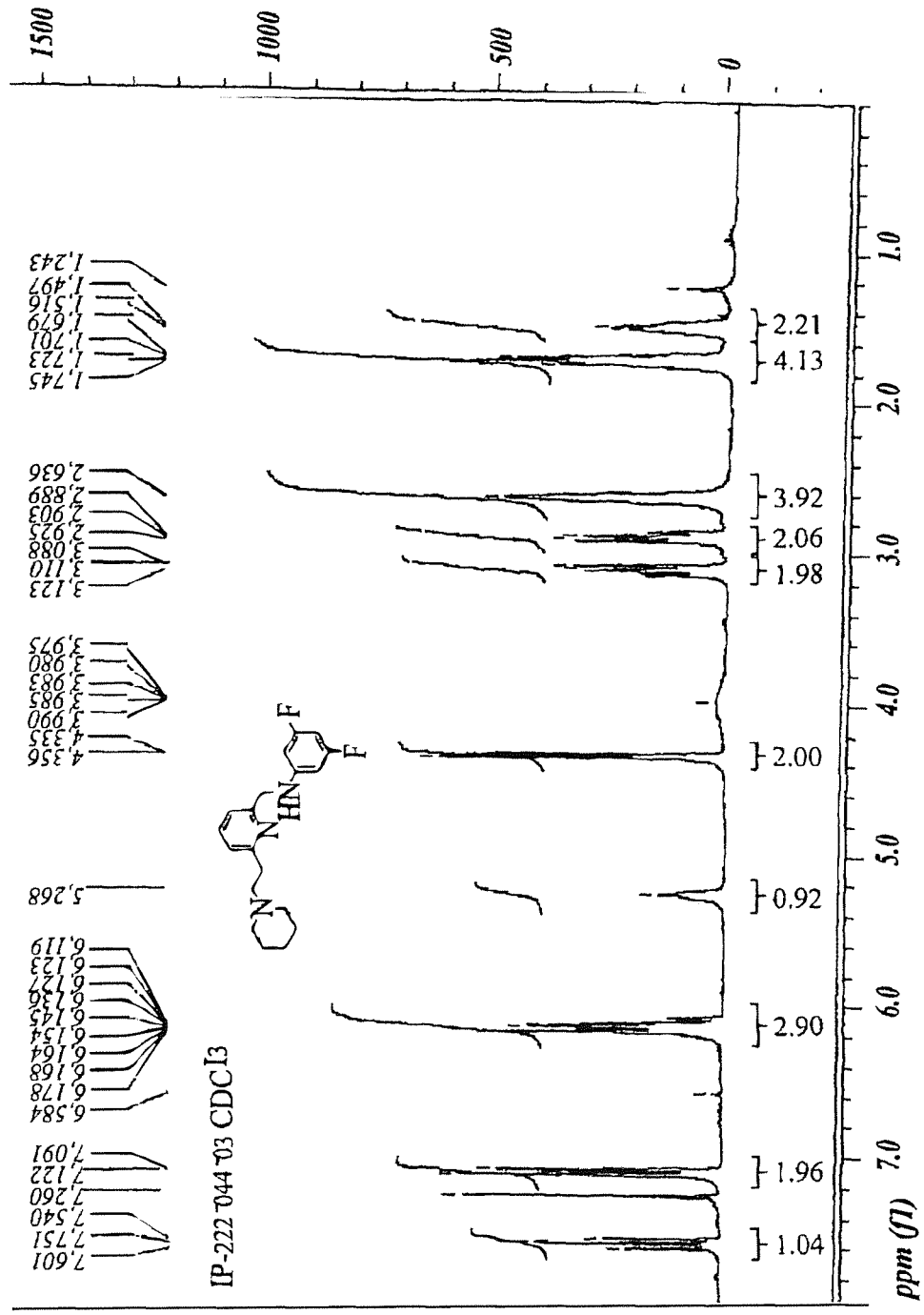
FIGS. 8A, 8B, 8C, 8D, 8E and 8F are NMR spectra of disclosed compounds.
Figure 8B:
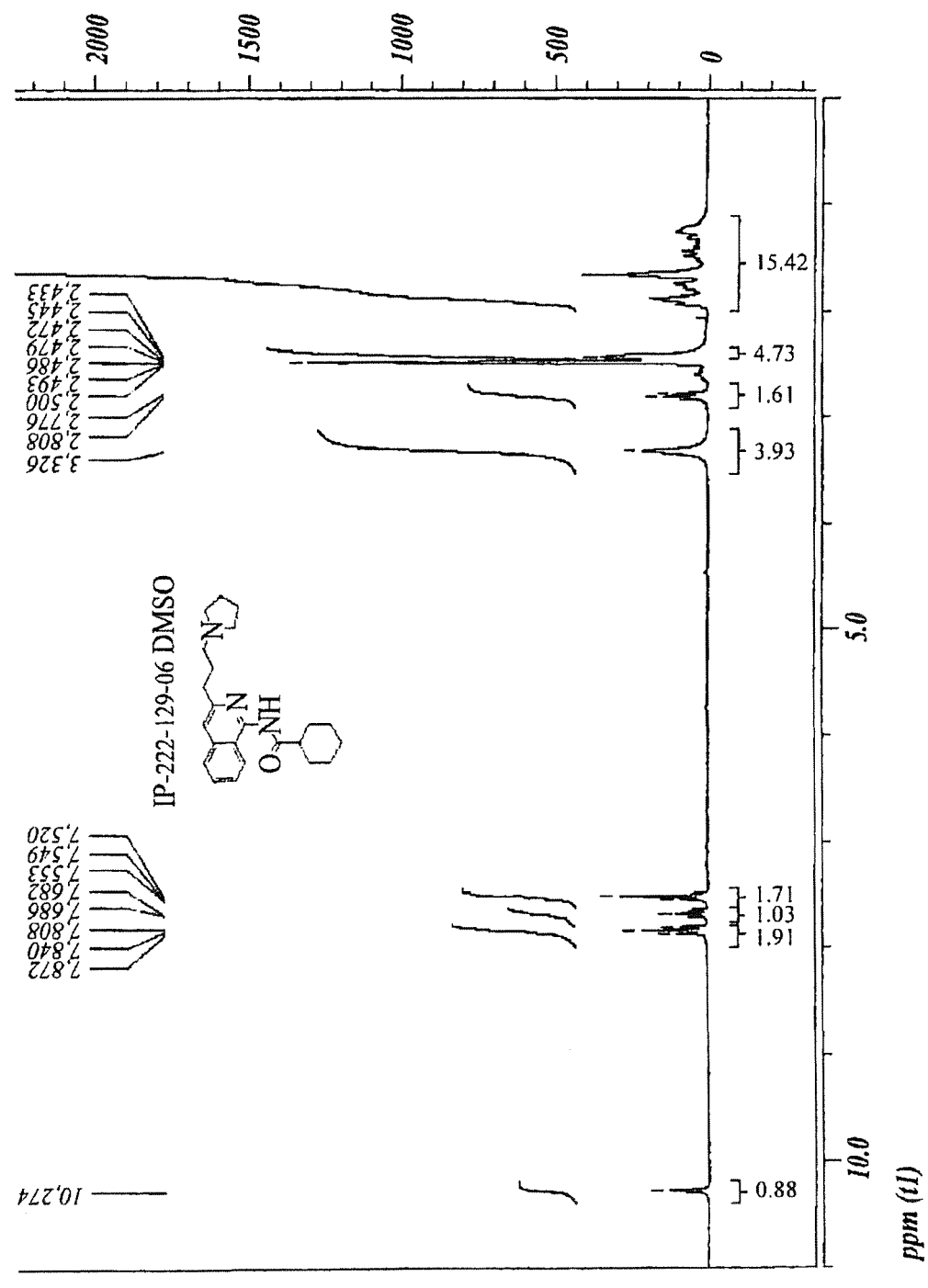
Figure 8C:
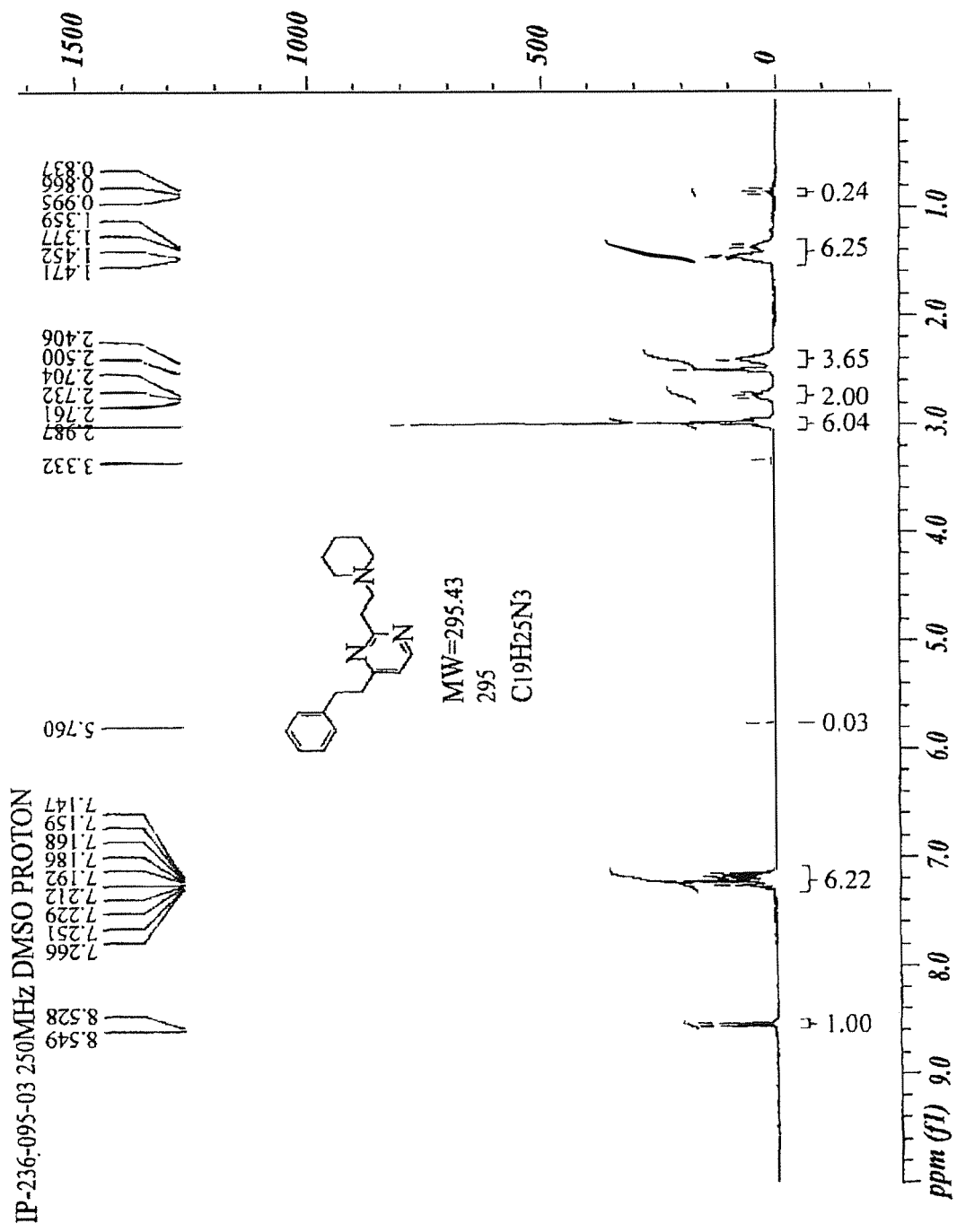
Figure 8D:
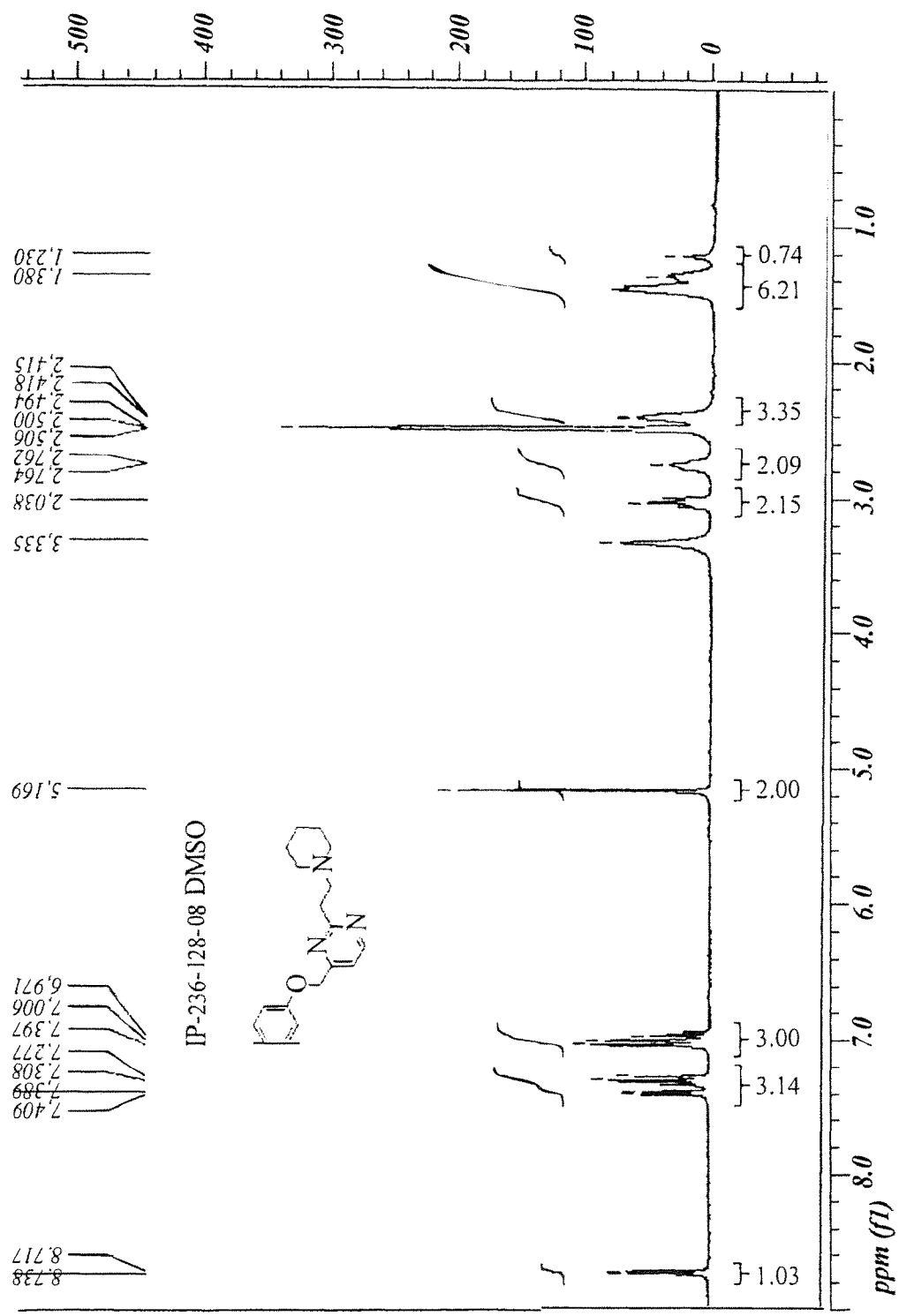
Figure 8E:
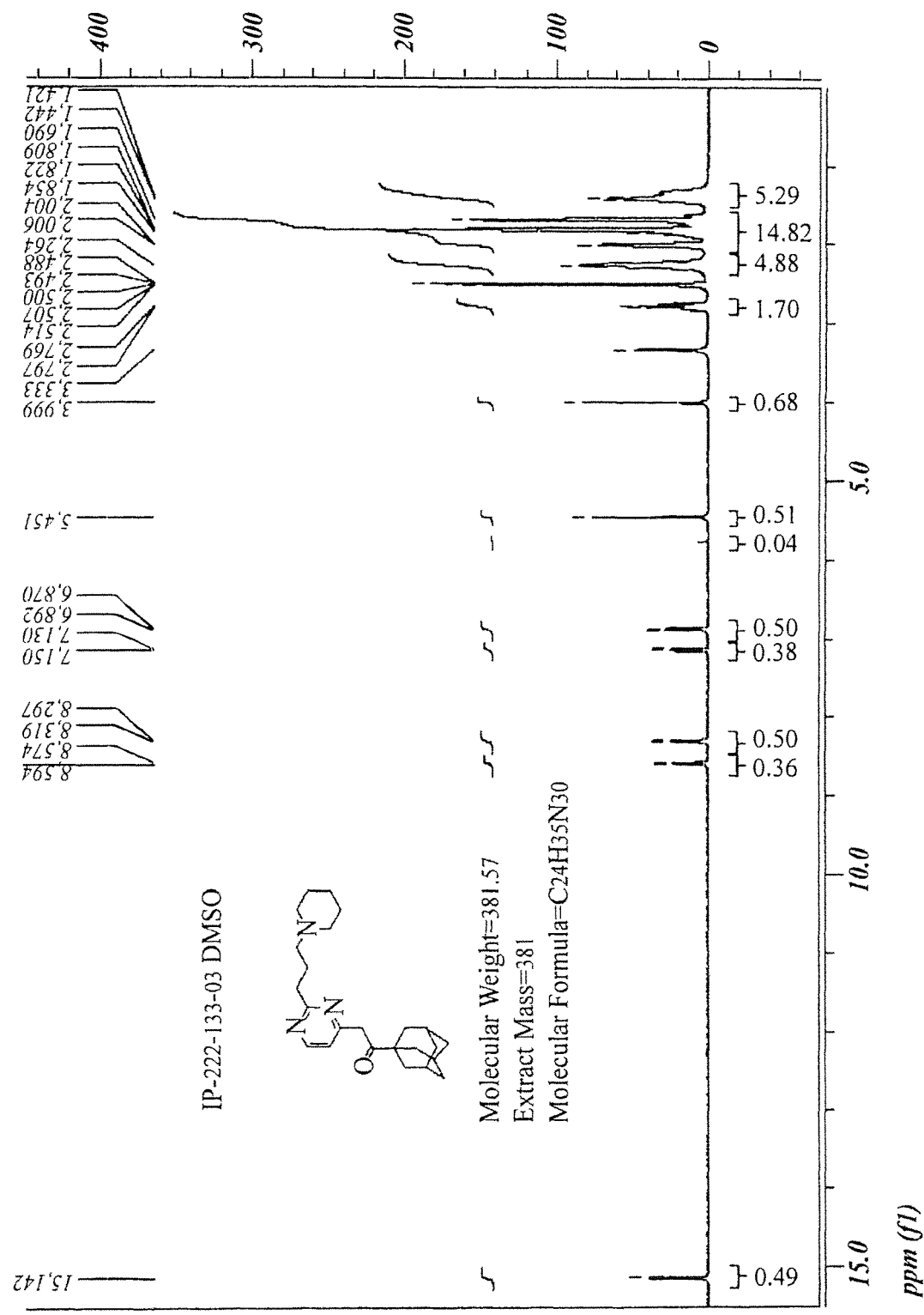
Figure 8F:
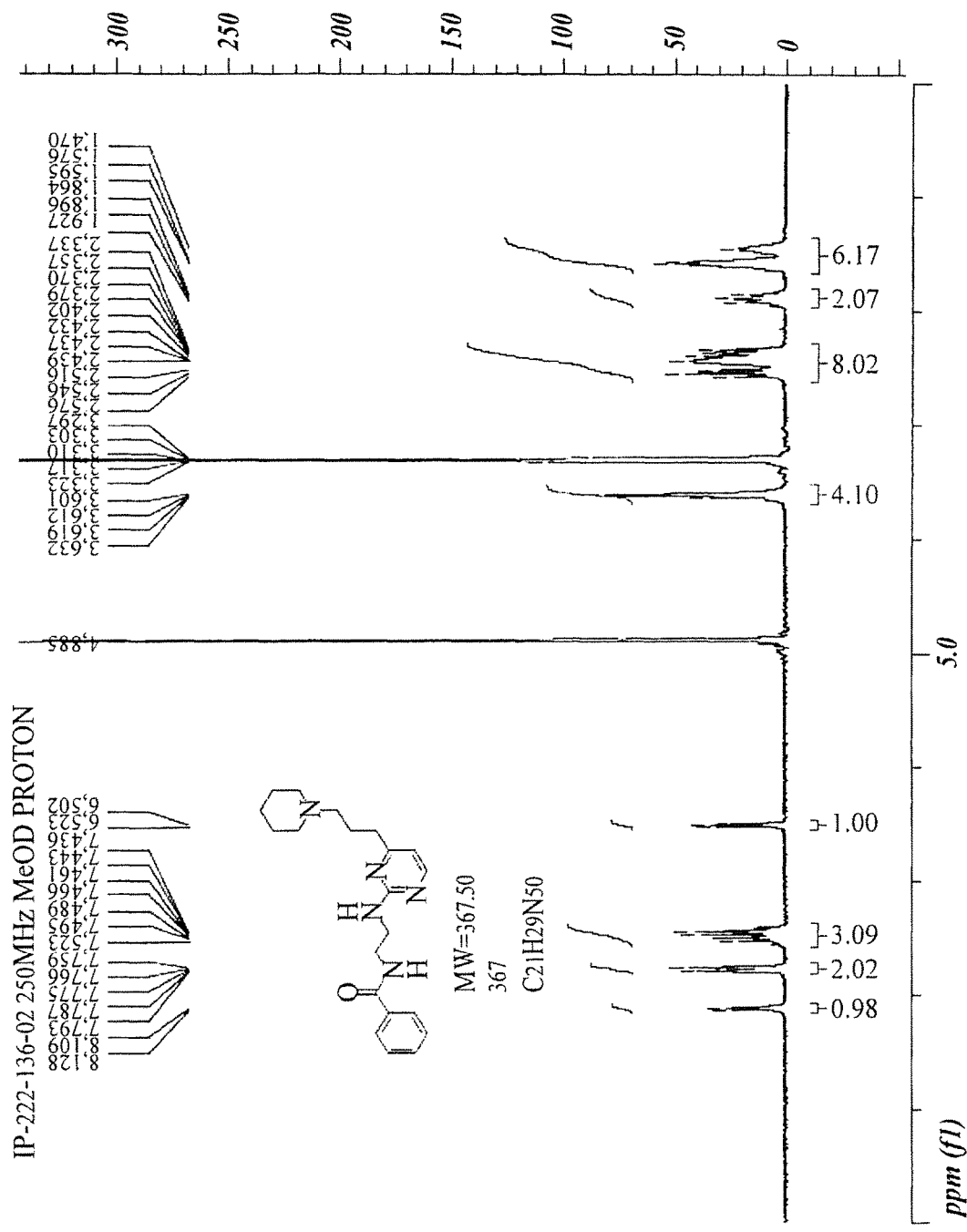

FIG. 1B compares inhibition of lymphocyte proliferation of the compounds (S4.1 and S4.4) with compounds (S3.1 and S3.4) at different concentrations. In vitro stimulation of lymphocytes using phytohematoglutinin (PHA) was compared to superantigen Enterotoxin B (SEB) stimulated T lymphocytes. Compounds were evaluated for their ability to fully suppress PHA stimulated lymphocyte proliferation and SEB stimulated proliferation partially. FIG. 1C shows other compounds tested in this assay. The compounds are identified in FIG. 7. FIG. 7 shows results of compounds tested using this assay, with percentage inhibition. The compounds were tests at 10 µm.

Lymphocytes were seeded in a 6 well plate ($1.0·10^7$/well), pretreated for 10 minutes with S3.1, S3.4 or dexamethasone and stimulated for 10 minutes with PHA. The experiment was stopped by adding a large volume of ice cold PBS to the cells. The suspension was transferred to a tube, briefly spinned down in a centrifuge and the supernatant removed. The pellet was lysed by adding cold lysisbuffer (0.1% NP40, 50 mM TrisHCl, 1 mM EDTA, 1 mM EGTA, 150 mM NaCl, 200 µM $Na_3VO_4$, 10 mM NaF and protease inhibitors) and incubating 20 minutes on ice.

To investigate the cell signaling events that are affected by treatment with S3.1 and S3.4, lysates were supplemented with sample buffer (188 mM Tris-$C_1$ (pH 6.8), 3% SDS, 30% glycerol, 0.01% bromophenol blue, 15% β-mercaptoethanol), heated to 95° C. for 5 minutes, cooled on ice and sonicated. Samples were then run on 10% SDS-PAGE gel, blotted to PVDF membrane and incubated with antibodies for phospho-Zap70 (Cell Signaling Technology (Beverly, Mass.)) and phospho-LAT (Cell Signaling Technology (Beverly, Mass.)). To show equal loading of the samples the blot was incubated with an antibody directed against beta-actin (Santa Cruz Biotechnology (Heidelberg, Germany)).

The kinase Lck acts as a gate keeper to T cell receptor (TCR) related signaling as it is one of the first and most up stream kinases to be activated upon stimulation of the TCR. As downstream signaling of the TCR is inhibited by S3.1 and S3.4 treatment interactions with Lck were investigated by immunoprecipitating Lck and blotting for Hsp90. For immunprecipitation experiments $1.0·10^7$ cells were used per condition. Cells were pelleted and lysed as described previously. The supernatant was precleared by adding 10 µl Protein A/G UltraLink resin (Pierce Biotechnology, Rockford, USA) for 30 minutes at 4° C. Beads were spinned down and discarded. Samples were incubated with 2 µg primary antibody and 25 µl beads for 2 hours at 4° C. Beads were washed with PBS, sample buffer was added and heated to 95° C. for 5 minutes.

Figure 2A:
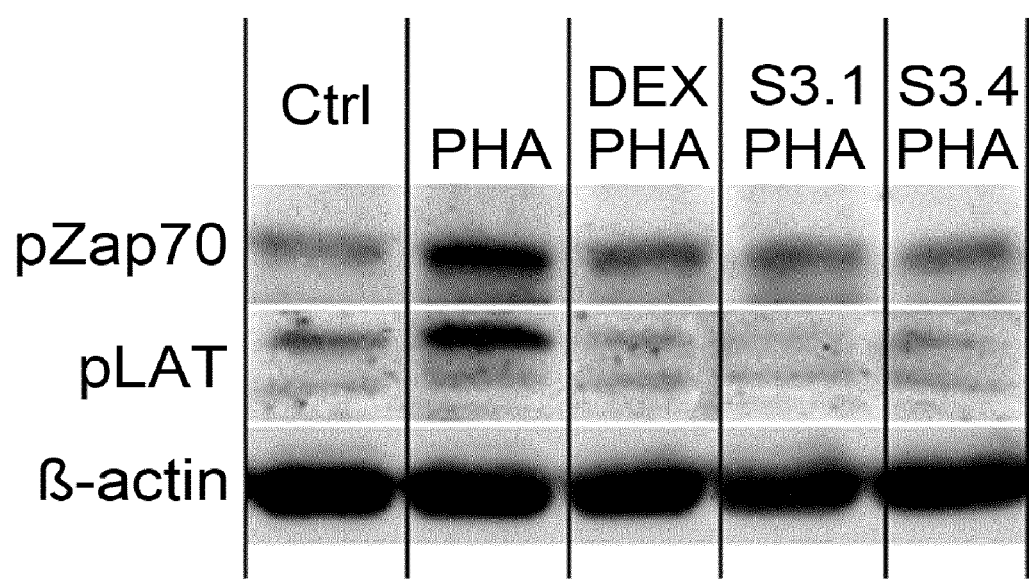
FIG. 2A depicts the effect of compounds S3.1 and S3.4 on T lymphocyte signal transduction
Figure 2B:
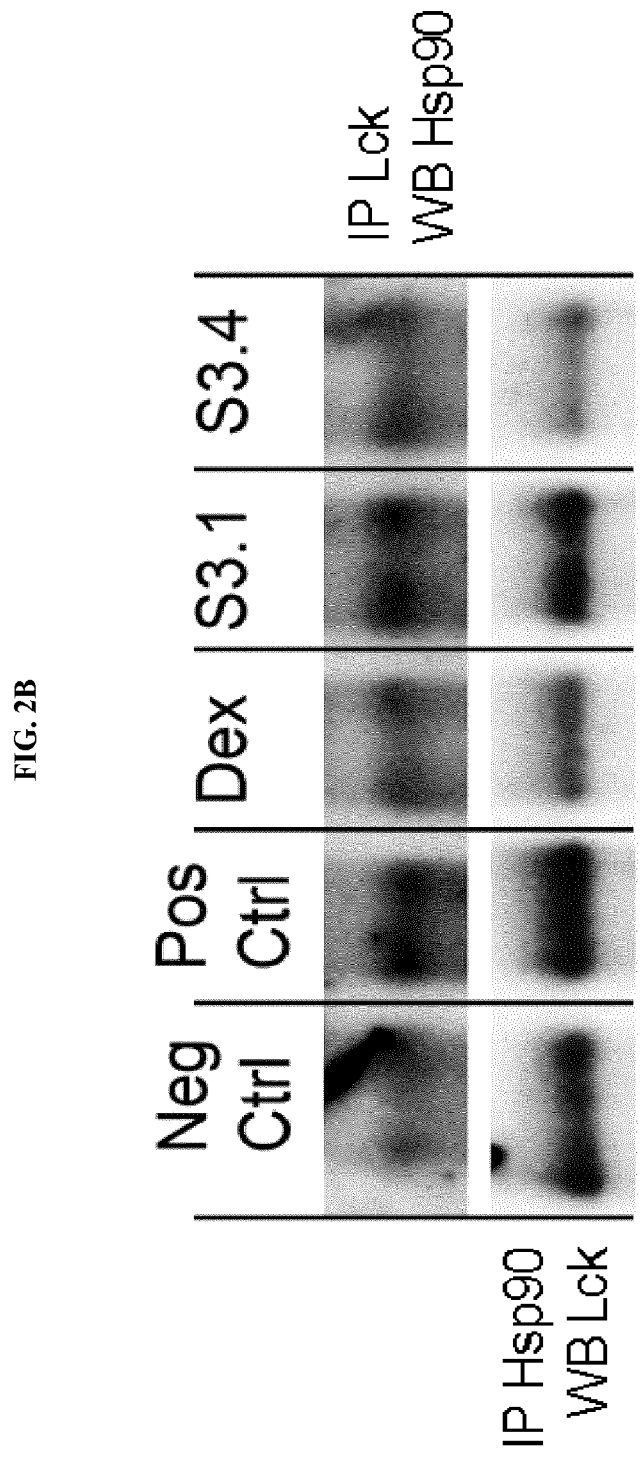
FIG. 2B depicts the effect of compounds S3.1 and S3.4 on the interaction between lymphocyte-specific protein tyrosine kinase (LCK) and its chaperone Hsp90.

The antiproliferative effect of compounds S3.1 and S3.4 is further reflected in the loss of T-Cell receptor (TCR) related signaling as was investigated by westernblot (see FIGS. 2A and 2B). Both the kinase Zap70 and the scaffolding protein LAT showed lower phosphorylation levels compared to a stimulated untreated control (FIG. 2A). Similar to the glucocorticoid (GC), dexamethasone treatment the interaction between lymphocyte-specific protein tyrosine kinase (LCK) and its chaperone Hsp90 was lost (FIG. 2B). This interaction protects LCK from degradation. Taken together this confirms an effect on TCR-proximal signaling, affecting LCK and downstream signaling events which ultimately result in the loss of proliferation and consequently a reduction of cytokine levels.

Example 8: Toxicity Evaluation (MTS Viability Assay on HELA Cervical Cancer Cells)

Compound S3.1 and S3.4 were tested against multiple cancer cell lines (HCT116, Hela, 293T) to assess toxicity using a MTS viability assay. Cell lines were treated for three days at 10 µM. Cells were seeded at multiple concentrations in a 96 wells plate in 100 µl medium. Next day S3.1 or S3.4 was added to each well at a concentration of 10 µM. To test cell viability, 20 µl of MTS solution (Promega, Madison, USA) was added to each well and incubated for four hours. Formation of the blue formazan was determined by measuring absorbance at 490 nm using a 96-well plate reader. Formazan is produced as MTS is reduced by the cells. Turnover of MTS correlates with the viability of the cells.

Figure 3:
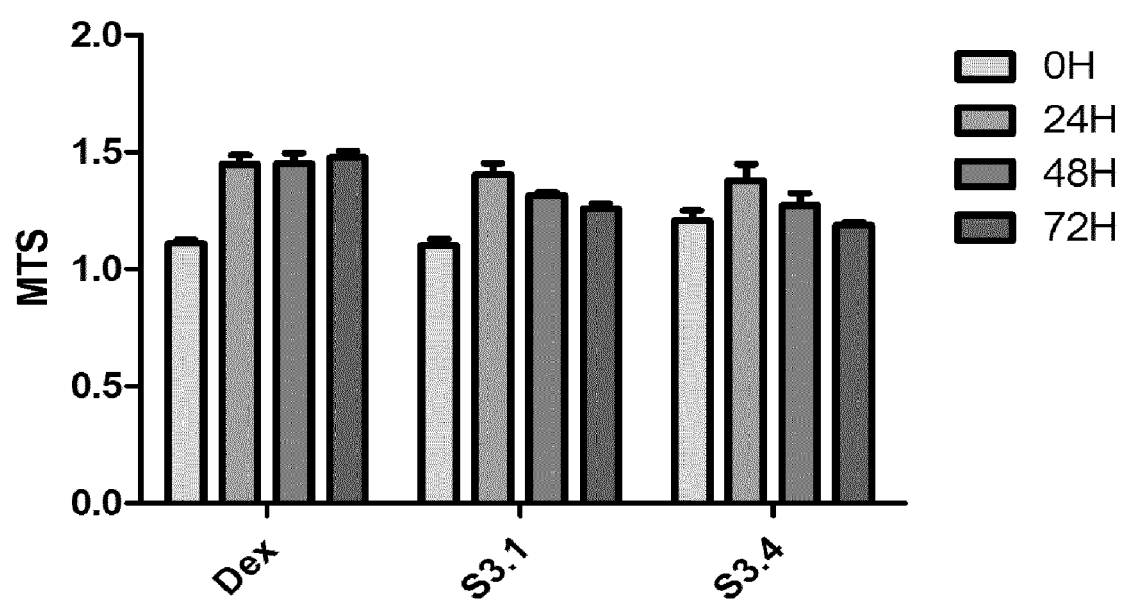
FIG. 3 depicts the effect of compounds S3.1 and S3.4 on HELA cervical cancer cells in a MTS viability assay.

As seen in FIG. 3, the compounds did not result in any negative effects on viability or proliferation.

Example 9: Comparison to Glucocorticoids and Evaluation of Side Effects

Because the compounds were selected for an effect similar to that of GC treatment and GC treatment is known to be accompanied by severe unwanted side effects, the compounds were screened for their ability to induce GC regulated genes. The tests were performed using a cell line which contains a GRE-luciferase reporter construct. GRE refers to glucocorticoid responsive element, a specific DNA sequence to which the ligand bound glucocorticoid receptor binds and luciferase is a gene coding for a protein which can catalyze the oxidation of luciferin, a reaction which is accompanied by bioluminescence.

293 GRE cancer cells were purchased from Panomics (Vignate-Milano, Italy). Cells were seeded in a 24 well plate at $1.10^5$ cells/well. After 48 hours cells were treated overnight with compounds or dexamethasone. Wells were aspirated and the cells lysed by adding 100 µl lysisbuffer (Promega, Madison, USA) to each well. 10 µl of the lysate was added to 100 µl of luciferase substrate. Produced light was measured by luminometer. To show that there is no transactivation of GR regulated genes (as would be the case with generic GR ligands) two well known side effects of corticosteroid treatment were investigated.

Figure 4A:
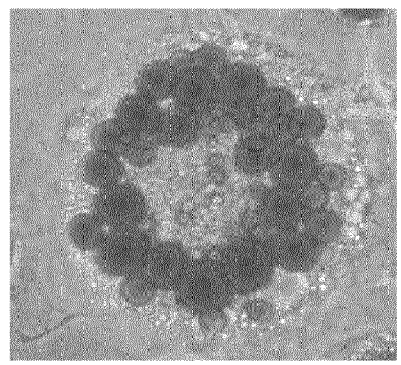
FIGS. 4A and 4B depict the effect of compounds S3.1 and S3.4 on differentiation of fibroblasts into adipocytes.
Figure 4B:
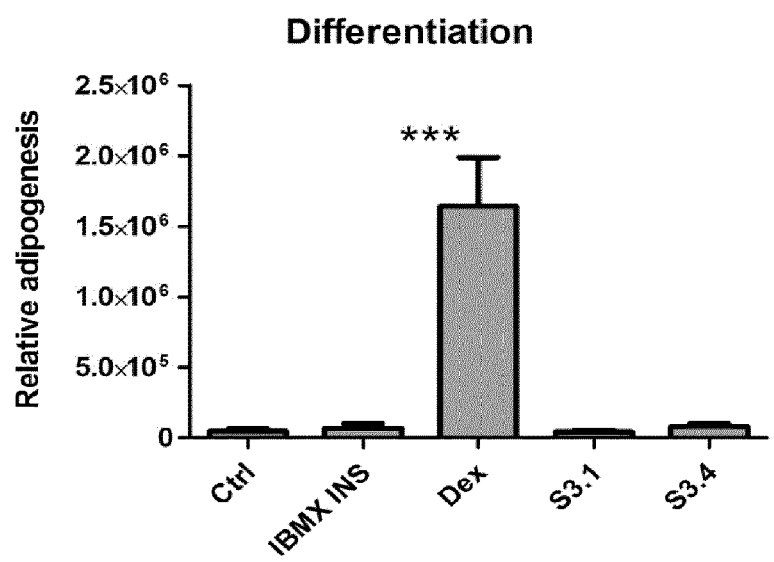
Figure 5A:
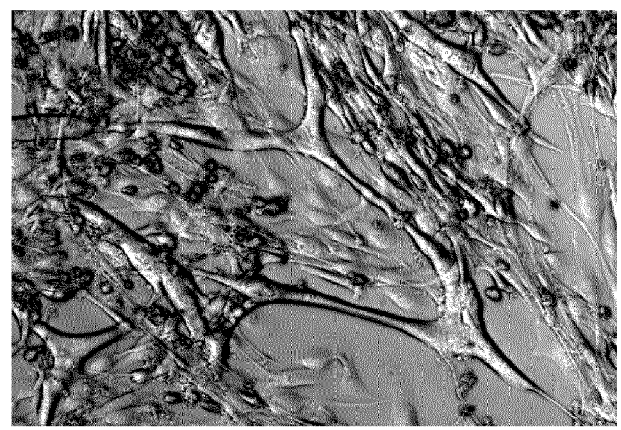
FIGS. 5A and 5B depict the effect of compounds S3.1 and S3.4 on muscle fiber thickness.
Figure 5B:
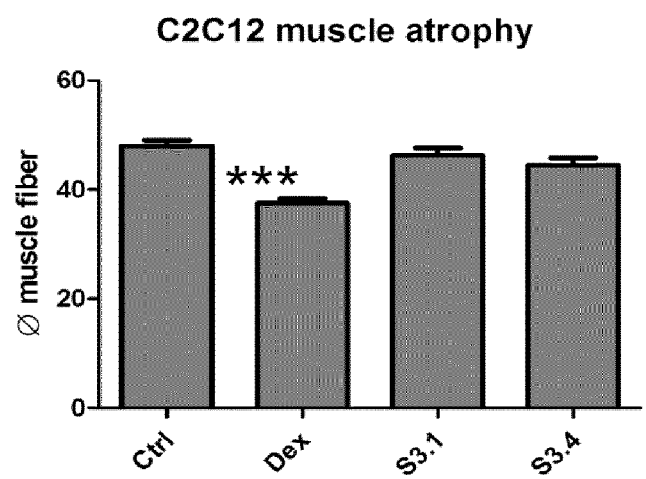
Figure 6:
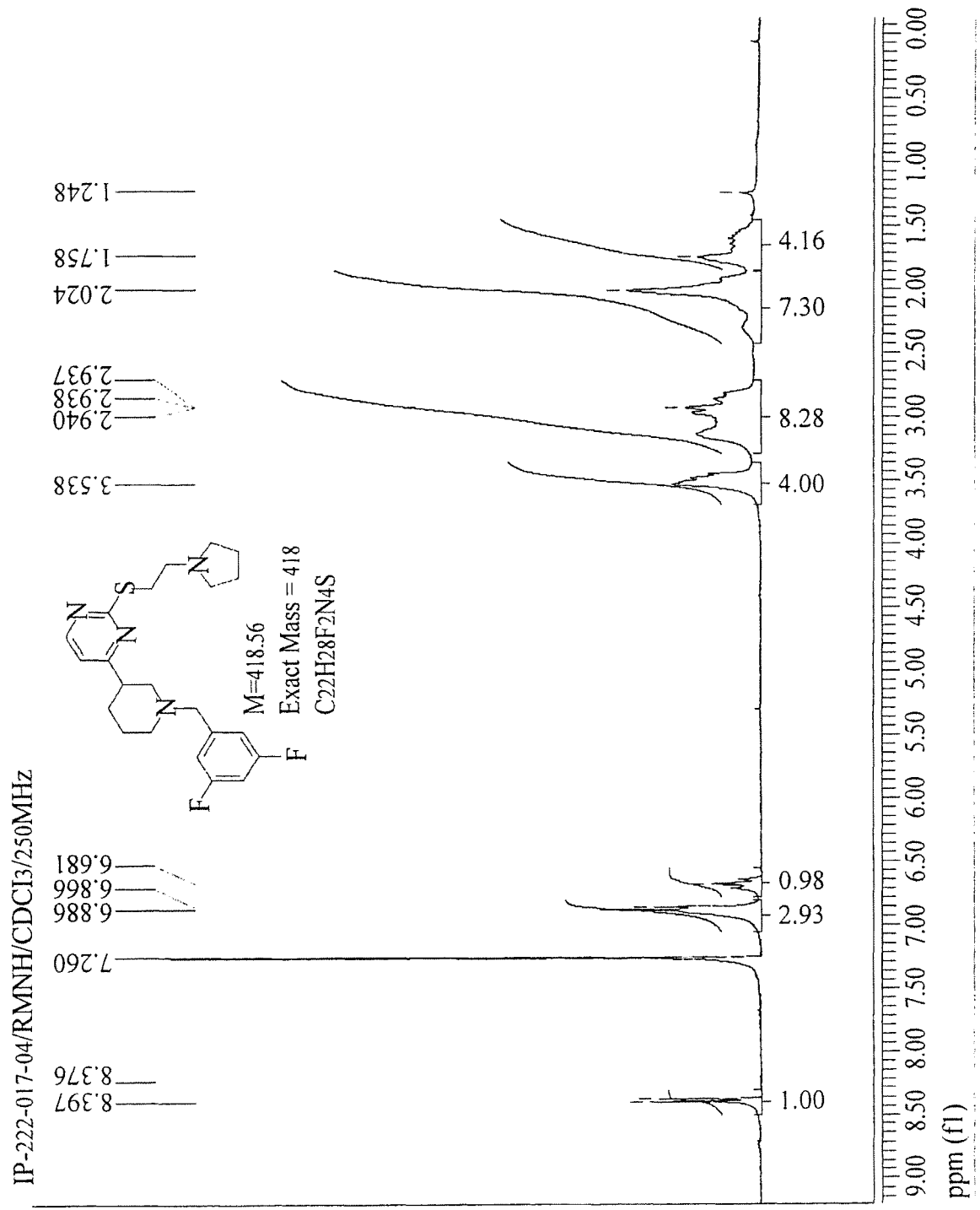
FIG. 6 is a NMR spectrum of compound 3.4.

FIGS. 4A and 4B Adipogenesis: FIGS. 4A and 4B show results after 3T3-L1 mouse fibroblasts were cultured in DMEM+10% FCS. After reaching full confluency the media was supplemented with insulin (1.6 µM), IBMX (0.5 mM) and dexamethasone or S3.1 or S3.4 (0.25 µM). After two days the media was replaced by growth medium containing insulin. After 6 days this medium was replaced by growth medium. A week later formation of lipid droplets was visualized by Oil Red O staining and quantified. Briefly; Cells were fixed for 15 minutes with 4% paraformaldehyde, washed with PBS, incubated in 4.4 mM Oil Red O/isopropanol solution for 10 minutes, washed 2×10 minutes with $H_2O$ and mounted in glycerol. FIGS. 5A and 5B show results after Muscle atrophy C2C12 mouse myoblasts were cultured in DMEM+5% FCS. When cells reached 90% confluency replace medium with DMEM supplemented with 5% HS and 1 µM insulin. After two days treat the cells with 4 µg/ml AraC. After one week cells were treated for 24 hours with 10 µM dexamethasone or S3.1 or S3.4. The experiment was stopped by fixing the cells overnight in cold 2% glutaraldehyde solution. This fixation method causes autofluorescence allowing easy visualization of the cells. Thickness of the formed muscle fibers was measured and quantified using Adobe photoshop CS4.

In the in vitro mouse myoblast cell line C2C12 assay, none of the compounds induce differentiation of fibroblasts into adipocytes (FIGS. 4A and 4B) or cause loss of muscle fiber thickness (FIGS. 5A and 5B), each of which are reported side effects of GC treatment.

Example 10

We have found that the binding of a disclosed compound, S3.4 can depend on the conformation of the glucocorticoid receptor. Compound S3.4 shows effect on lymphocyte proliferation. The following assay was conducted to measure binding directly in activated T cells using S3.4 to compete with radiolabeled dexamethasone.

1. Isolate Peripheral Blood Lymphocytes
2. Prepare conditions/$10^6$ cells in a total volume of 1 ml.
3. Stimulate cells for 15 minutes with PHA at 37° C.
4. Add compound plus [3H]dexamethasone
5. Incubate for 1 hour at room temperature
6. Spin cells down at 400×g for 5 minutes
7. Discard supernatant
8. Wash in ice cold PBS for 30 minutes at rollerbench/inverter.
9. Repeat step 6-8
10. Dissolve pellet in scintillation liquid
11. Measure Activity: 1 mCi Activity Concentration: 50-90 Ci/mmol (1.85-3.33 TBq/mmol)

Concentration: 1 mCi/ml (37 MBq/ml)

Figure 9A:
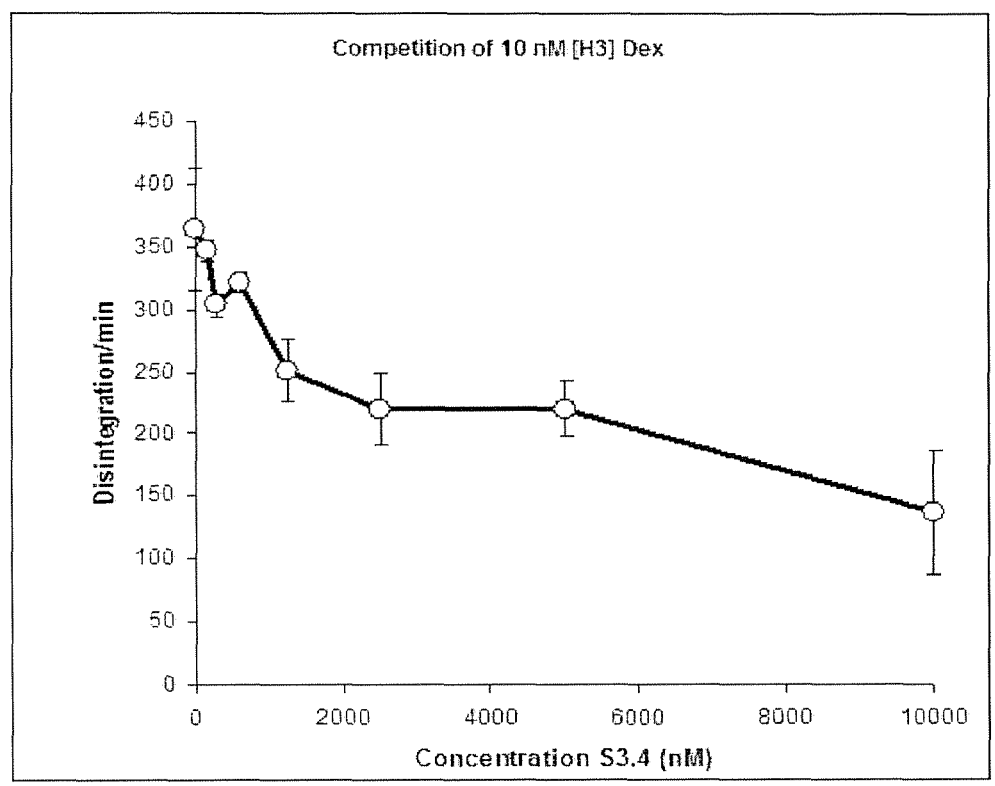
FIGS. 9A and 9B depict results of competition/binding assay using compound 3.4 (A) and compound 3.4 with dexamethasone (Dex) and hydrocortisone (HC).
Figure 9B:
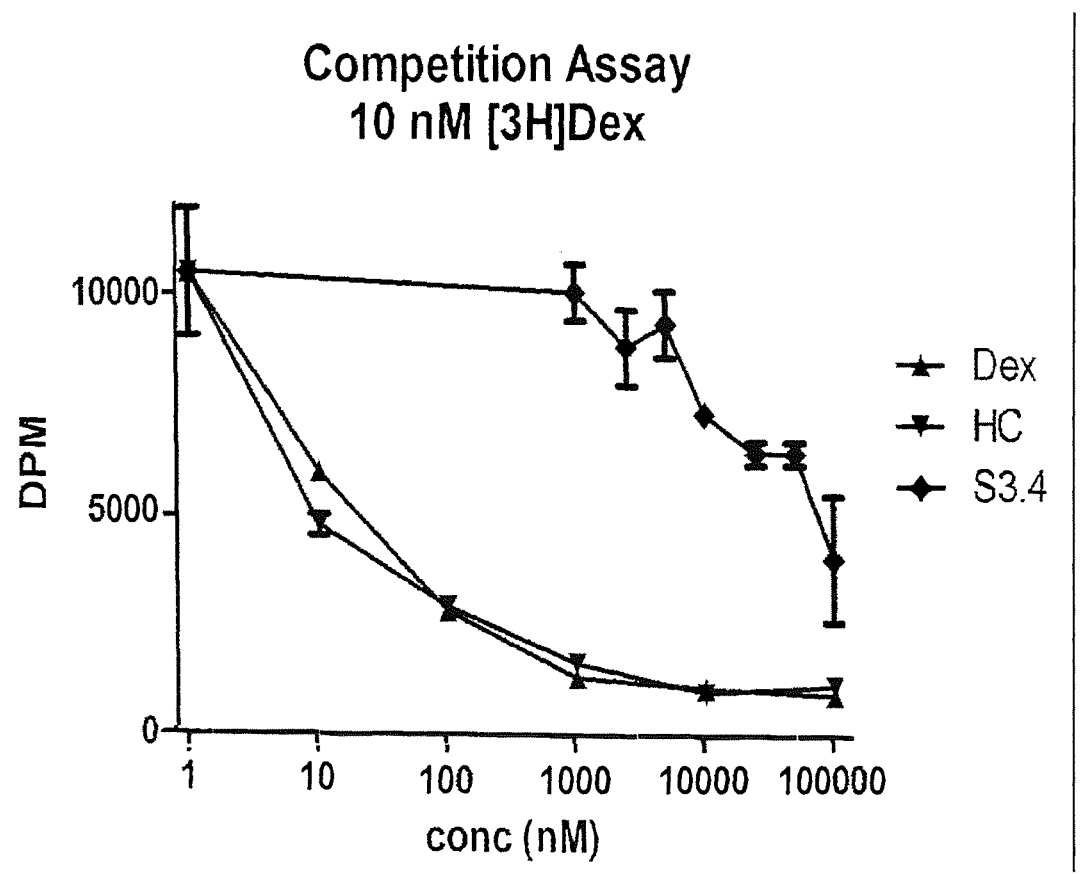

FIGS. 9A and 9B indicate results using this assay with compound S3.4 (compound 3.4), dexamethasone (Dex) and hydrocortisone (HC). Without being bound by theory, a hypothesis is that the glucocorticoid receptor (GR) takes on a specific conformation when bound in a complex to Lck. The GR is only associated to Lck when lymphocytes are stimulated. Therefore the cells in this experiment need to be stimulated before the compound is added.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:

1. A heterocyclic compound selected from the group consisting of:

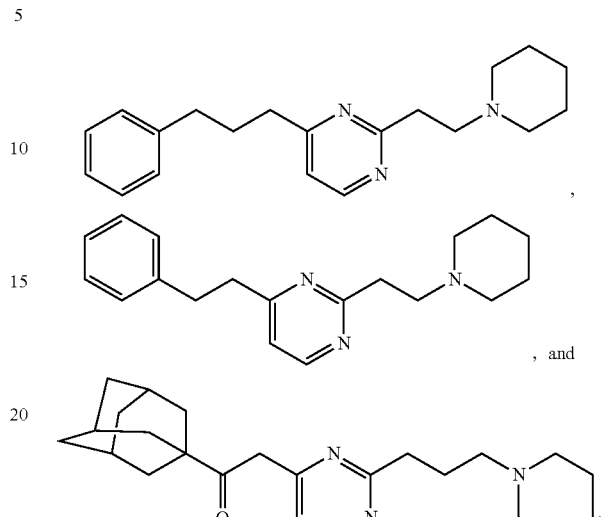

or a pharmaceutically acceptable salt thereof.

2. The heterocyclic compound of claim 1, wherein the compound is:

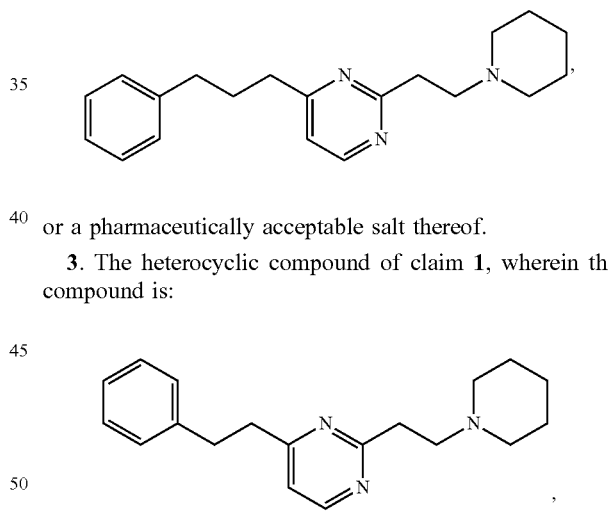

or a pharmaceutically acceptable salt thereof.

3. The heterocyclic compound of claim 1, wherein the compound is:

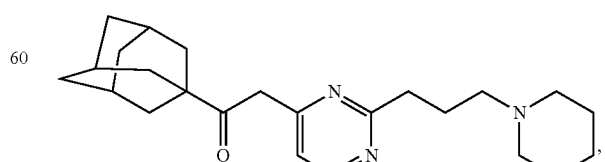

or a pharmaceutically acceptable salt thereof.

4. The heterocyclic compound of claim 1, wherein the compound is:

or a pharmaceutically acceptable salt thereof.

5. A pharmaceutical composition comprising:
a compound selected from the group consisting of:

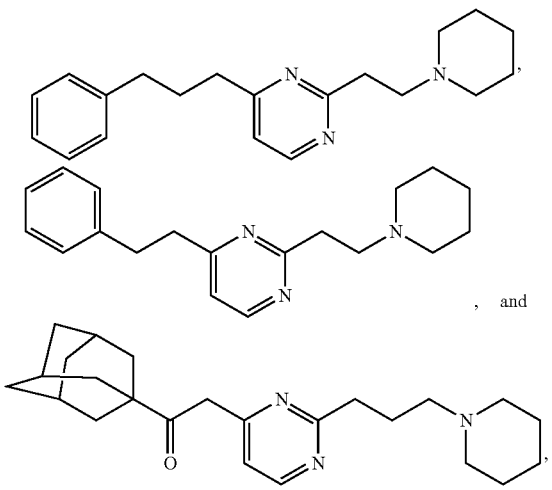

or a pharmaceutically acceptable salt thereof, and
a pharmaceutically acceptable adjuvant or excipient.

6. The pharmaceutical composition of claim 5, wherein the compound is:

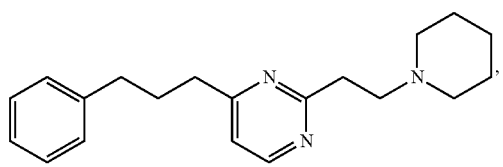 [SMILES: c1ccc(CCCc2ccnc(CCN3CCCCC3)n2)cc1]

or a pharmaceutically acceptable salt thereof.

7. The pharmaceutical composition of claim 5, wherein the compound is:

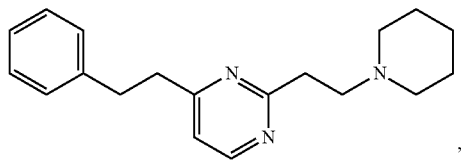 [SMILES: c1ccc(CCc2ccnc(CCN3CCCCC3)n2)cc1]

or a pharmaceutically acceptable salt thereof.

8. The pharmaceutical composition of claim 5, wherein the compound is:

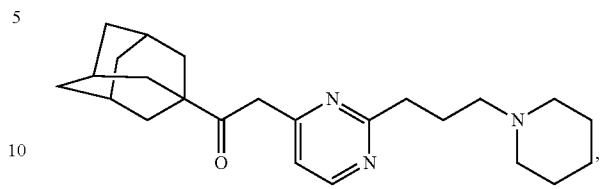

or a pharmaceutically acceptable salt thereof.

9. A method of treating an immune inflammatory disease or disorder in a subject in need thereof, the method comprising administering to the subject a pharmaceutically effective amount of the heterocyclic compound of claim 1, wherein the immune inflammatory disease or disorder is selected from the group consisting of Crohn's disease, ulcerative colitis, a rheumatic disorder, psoriasis, and an allergy.

10. The method of claim 9, wherein the allergy is contact dermatitis.

11. The method of claim 9, wherein the allergy is atopic dermatitis.

12. A method of treating an immune inflammatory disease or disorder in a subject in need thereof, the method comprising administering to the subject a pharmaceutically effective amount of the pharmaceutical composition of claim 5, wherein the immune inflammatory disease or disorder is selected from the group consisting of Crohn's disease, ulcerative colitis, a rheumatic disorder, psoriasis, and an allergy.

13. The method of claim 12, wherein the allergy is contact dermatitis.

14. The method of claim 12, wherein the allergy is atopic dermatitis.

* * * * *